(12) United States Patent
Bierbach et al.

(10) Patent No.: US 10,377,784 B2
(45) Date of Patent: *Aug. 13, 2019

(54) DESIGN, SYNTHESIS, AND BIOLOGICAL ACTIVITY OF PLATINUM-BENZ[C]ACRIDINE HYBRID AGENTS AND METHODS ASSOCIATED THEREWITH

(71) Applicant: Wake Forest University, Winston-Salem, NC (US)

(72) Inventors: Ulrich Bierbach, Winston-Salem, NC (US); Amanda J. Pickard, New York, NY (US)

(73) Assignee: WAKE FOREST UNIVERSITY, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/033,940

(22) Filed: Jul. 12, 2018

(65) Prior Publication Data

US 2018/0319832 A1 Nov. 8, 2018

Related U.S. Application Data

(63) Continuation of application No. 15/126,422, filed as application No. PCT/US2015/020635 on Mar. 15, 2015, now Pat. No. 10,023,599.

(60) Provisional application No. 61/953,765, filed on Mar. 15, 2014.

(51) Int. Cl.
*A61K 47/54* (2017.01)
*C07F 15/00* (2006.01)

(52) U.S. Cl.
CPC ........ *C07F 15/0093* (2013.01); *A61K 47/545* (2017.08)

(58) Field of Classification Search
CPC .......................... C07F 15/0093; A61K 47/545
See application file for complete search history.

(56) References Cited

U.S. PATENT DOCUMENTS

| | | | |
|---|---|---|---|
| 2,981,731 A | 4/1961 | Moore et al. |
| 2012/0039800 A1 | 2/2012 | Bierbaum |

FOREIGN PATENT DOCUMENTS

| | | |
|---|---|---|
| WO | 1996018611 A2 | 6/1996 |
| WO | 2013033430 A1 | 3/2013 |
| WO | 2013103707 A1 | 7/2013 |

OTHER PUBLICATIONS

Ackerman et al., "Preparation and Screening of Aminoacridines for Induction of Lung Tumor Fluorescence in Rats," Journal of Medicinal Chemistry, American Chemical Society (Mar. 1968); 11:315-321.
Shortridge et al., "The Action of Aminobenzacridines on the Furth Rat Leukaemia," British Journal of Cancer, (Dec. 1, 1969); 23(4):825-832.
Groundwater et al., Benzophenanthrolines and related fused acridines, preparation thereof, and use in carcinoma treatment, retrieved from STN Database Accession No. 1996:509382 (1 page).
PUBCHEM-CID-4204622 (Created: Sep. 13, 2005) (14 pages).

*Primary Examiner* — Joseph R Kosack
(74) *Attorney, Agent, or Firm* — Fox Rothschild LLP

(57) ABSTRACT

The present invention relates to the compounds of formula (I), pharmaceutically acceptable salts, and solvates thereof, wherein the various substituents are as defined herein. The compounds, solvates and salts thereof of Formula (I) are effective as anti-cancer compounds.

19 Claims, 4 Drawing Sheets

DESIGN, SYNTHESIS, AND BIOLOGICAL ACTIVITY OF PLATINUM-BENZ[C]ACRIDINE HYBRID AGENTS AND METHODS ASSOCIATED THEREWITH

This application is a Continuation of U.S. patent application Ser. No. 15/126,422, filed Sep. 15, 2016, which is the U.S. National Phase of International Application No. PCT/US2015/20635, filed Mar. 15, 2015, which claims priority under 35 USC 119(e) to U.S. Provisional Application No. 61/953,765 filed Mar. 15, 2014. Each of these applications are incorporated herein by reference in their entirety.

FIELD OF THE INVENTION

The present invention was supported by NIH-NCI grant contract number CA101880. Accordingly, the Federal Government has rights in the present invention.

BACKGROUND OF THE INVENTION

Since the FDA approval of cisplatin in 1978, platinum chemotherapy has been the mainstay for a multitude of solid malignancies. The limiting factors of cisplatin's efficacy in a wide variety of cancers has been its systemic toxicity and drug resistance after treatment. The development of second-generation cisplatin drugs, such as FDA approved carboplatin, oxaliplatin, nedaplatin, lobaplatin, and heptaplatin, has addressed some, but not all of the limitations of cisplatin.

A new generation of platinum-based chemotherapy, platinum-acridine hybrid agents, are classical double-stranded DNA intercalators that produce a mono-functional platinum adduct with guanine nucleobases. This mechanism of action, differing from the DNA cross-linking produced by the first and second-generation platinum drugs, has shown increased cytotoxicity and activity in vivo in non-small-cell lung cancer. These drugs are able to elude many of the DNA repair mechanisms by decreasing the structural perturbations that occur upon platination of DNA, as well as have decreased reactivity with sulfur-based nucleophiles, such as glutathione. The overarching issue with platinum-based chemotherapy to date is their inherent, and indiscriminate genotoxicity, resulting in high systemic toxicity.

In an effort to reduce genotoxicity it is important to determine cancer-specific targets and develop platinum-based chemotherapy with decreased non-specific binding to genomic DNA. Classical DNA-targeted drugs employ their cytotoxicity by cross-linking, intercalating, inducing double-strand breaks, groove-binding, and inhibiting or enhancing protein-DNA complexes with genomic double-stranded DNA. New and exciting DNA targets, which could result in decreased systemic toxicity, are DNA secondary structures. These secondary structures, such as G-quadruplexes, triplex DNA, and i-motifs, could provide the key to more selective cancer chemotherapies.

The importance of non-classical DNA secondary structures during transcription has been demonstrated. Negative supercoiling of B-form DNA has been shown to cause local unwinding, which in the case of the c-Myc oncogene promotor, could allow for G-quadruplex or i-motif formation. Due to the limitations of i-motif formation, which involve non-physiological conditions, G-quadruplex formation is a much more valuable target to restricting gene restriction in this promotor region. Similarly, putative G-quadruplex forming regions have been found in the promotor regions of the Bcl-2, c-Kit, RET, VEGF, Hif-1α, PDGFA, c-Myb and KRAS genes, all of which have implications in cancer progression. In addition, putative G-quadruplex forming sequences have been discovered at the telomeric repeat and in the ribosomal DNA (rDNA) found in nucleolar organizer regions (NORs).

Important factors determining specificity to various types of DNA secondary structures are geometry and electrostatic interactions. G-quadruplexes, for instance, have an affinity for drugs containing an extended aromatic moiety, due to their inherent ability to π-π stack with the terminal G-tetrads that make up the G-quadruplex structure. This fact, however, is also true of agents preferring to intercalate Watson-Crick DNA, due to the π-π interactions formed with the hydrogen-bonded bases found in the base-stack. To circumvent this issue with specificity, chemotherapeutic agents must be developed that are too bulky to intercalate the base-stack, such as with 2,7-di-tert-butyl proflavine, therefore shifting its π-π stacking potential to non-classical secondary DNA structures. Derivatives of ethidium bromide, a classical intercalator of Watson-Crick base pairs, suggest that intercalative molecules can be altered to produce G-quadruplex and triplex selectivity. Also, decreasing the positive charge of a drug has been shown to decrease its unwanted interactions with duplex versus G-quadruplex DNA.

One major drawback of platinum-based chemotherapies (including platinum-acridines) is their high level of toxicity when administered systemically. Systemic toxicity is the result of unfavorable pharmacokinetic and pharmacodynamic parameters and off-target reactivity. Dicationic, hydrophilic platinum-acridines, although highly effective against solid tumors, have two major disadvantages: they are excreted from circulation too rapidly through the kidneys (producing high nephrotoxicity) and show indiscriminate reactivity with cellular DNA leading to a high level of non-specific genotoxicity. Both factors most likely contribute to the low tolerability of platinum-acridines as observed in test animals. In an effort to reduce the genotoxicity of a DNA-targeted pharmacophore it is important to determine cancer-specific targets at the nuclear level. Classical DNA-targeted drugs produce their cytotoxicity by cross-linking, intercalating, inducing double-strand breaks, groove-binding, and inhibiting or enhancing protein-DNA complexes with genomic double-stranded DNA.

New and exciting DNA targets, which could result in decreased systemic toxicity, are DNA secondary structures. These secondary structures, such as G-quadruplexes, triplex DNA, and i-motifs, could provide the key to selective cancer chemotherapy. Important factors determining specificity to various types of DNA secondary structures are geometry and electrostatic interactions. G-quadruplexes, a validated cancer target, for instance, have a high affinity for drugs containing an extended aromatic moiety, due to their inherent ability to π-π stack with the terminal G-tetrads that make up the G-quadruplex structure. This fact, however, is also true of agents preferring to intercalate Watson-Crick DNA, due to the π-π interactions formed with the hydrogen-bonded bases found in the base-stack. To circumvent this issue with specificity, chemotherapeutic agents must be developed that are incompatible with classical intercalation into the double-helical base-stack, therefore shifting their π-π stacking potential to non-classical secondary DNA structures.

BRIEF SUMMARY OF THE INVENTION

Newly designed compounds modeled from the platinum-acridine hybrid agents will display increased planar aromatic surface area and/or increased steric bulk around the chromophore and a decreased pKa of the endocylic nitrogen resulting in a decreased overall positive charge.

In an embodiment, the present invention relates to computational studies and a modular library to determine suitable alternatives to classic Pt-acridine hybrid agents. The compounds of the present invention display newly developed criteria to decrease off-target binding and systemic toxicity. From this preliminary screening tool, a new Pt-benz [c]acridine hybrid agent was developed, which displayed a more favorable pKa and lipophilicity, while still maintaining nanomolar cytotoxicities in highly aggressive NSCLC (non-small-cell lung cancer) lines. The use of modular libraries in assisting in the development of platinum cytotoxic agents is valuable. In an embodiment, the development of the methodologies described herein have opened a new class of platinum hybrid agents that have been shown to have promise for treating various types of cancer.

In an embodiment, the present invention relates to redesigned platinum-intercalators into more DNA structure-selective agents while improving their drug-like properties in circulation (reduced charge/basicity and increased lipophilicity). In an embodiment, new platinum-chromophore hybrid agents, platinum-benz[c]acridines, have been designed, synthesized, fully characterized, and investigated for their biological activity in non-small-cell lung cancer (NSCLC). The compounds of the present invention display a more favorable overall charge and lipophilicity for appropriate bioaccumulation and cellular uptake when compared to the prototypical platinum-acridine hybrid agents (P1-A1). Both P1-B1 and P1-B2 have displayed the ability to fold and irreversibly platinate G-quadruplex DNA, which is a new target of interest. Due to their decreased overall charge and increased planar aromatic surface area, they have the potential to increase G-quadruplex selectivity over that of P1-A1. P1-B1, in particular, maintained nanomolar cytotoxicity levels in multiple aggressive NSCLC lines, much like the prototype P1-A1. Due to the targeting of cancer-cell specific targets, such as G-quadruplex DNA and RNA, the platinum benz[c]acridines should be able to overcome the limitations of the platinum-acridine hybrid agents.

DETAILED DESCRIPTION OF THE INVENTION

Figure 1:
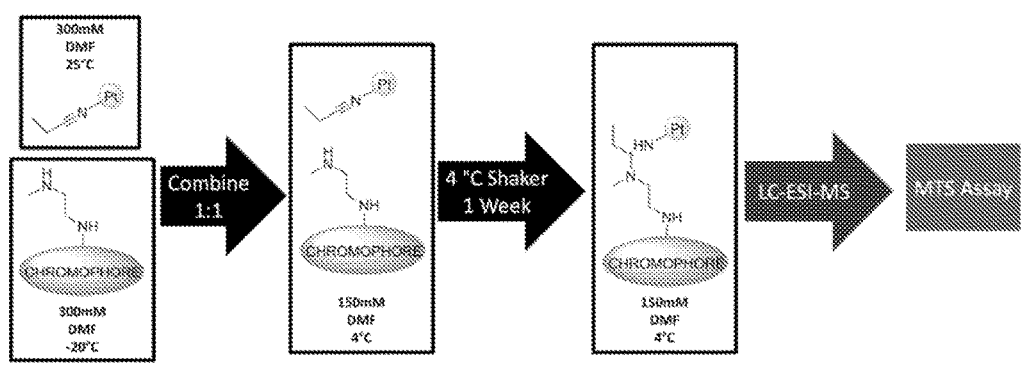
FIG. 1 shows the conditions and procedure for modular library screening.

In an embodiment, the present invention relates to a new treatment for intractable cancer. In an embodiment, the present invention relates to the discovery of a new platinum-benzacridine pharmacophore that shows potent activity in vitro against several notoriously chemoresistant non-small cell lung cancer (NSCLC) lines. In an embodiment, the present invention relates to new types of compounds (P1-B1 and P1-B2) that were modified from previously reported agents (e.g., P1-A1), which proved to maintain nanomolar cytotoxicity in NCI-H460 NSCLC. The chemical compositions of P1-B1 and P1-B2 are distinct from that of the prototype. The platinum-benz[c]acridines possess structural design features capable of overcoming the limitations of classical platinum-acridine agents by decreasing systemic toxicity.

In an embodiment, the present invention relates to the compounds of Formula I, and pharmaceutically acceptable salts and solvates thereof:

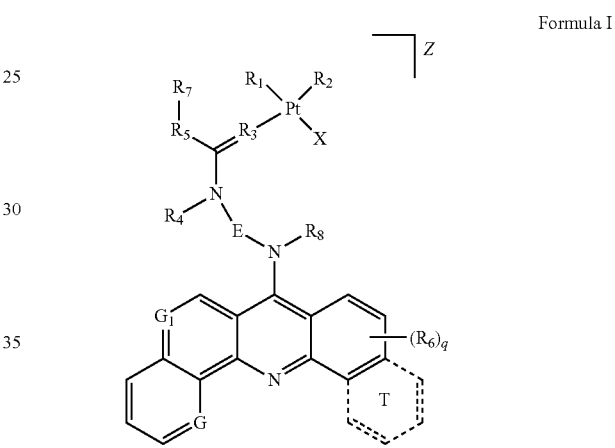

Formula I wherein X is halo, OC(O)R$_9$, nitrate or sulfate;

R$_1$ and R$_2$ are amino groups or together with the platinum atom to which they are attached, R$_1$ and R$_2$ form the ring —NH$_2$—(CH$_2$)$_v$—NH$_2$— wherein v is 1, 2, 3, or 4 or R$_1$ and R$_2$ together can be any of the following groups a-h;

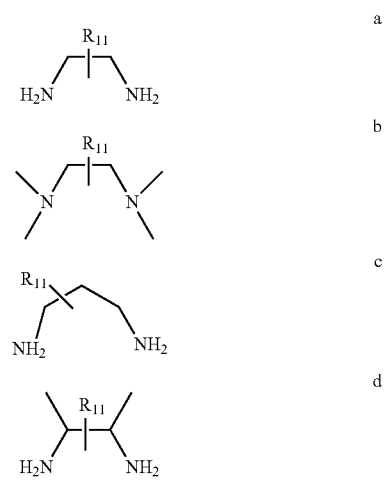

-continued

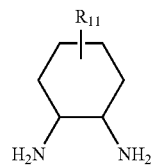
e

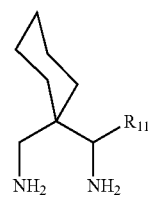
f

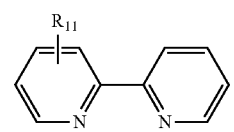
g

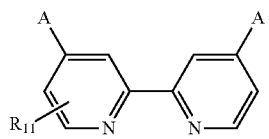
h wherein A is H, —CH$_3$, —OCH$_3$, CF$_3$ or NO$_2$;
R$_3$ is —N(R$_{26}$)—; wherein R$_{26}$ is hydrogen or C$_1$-C$_6$alkyl;
R$_4$ is hydrogen, C$_{1-6}$ alkyl, or CH$_2$—R$_{12}$;
R$_6$ is independently an amino, a nitro, —NHC(O)(R$_{10}$), —NHC(O)O(R$_{10}$), —C(O)NHR$_{10}$, —OC(O)NHR$_{10}$, or halo;
R$_{10}$ is hydrogen, C$_{1-6}$ alkyl, phenyl, naphthyl, C$_{3-6}$ cycloalkyl, norbornyl, or adamantyl;
q is 0, 1, or 2;
R$_5$ is a direct bond, —NH— or C$_1$-C$_6$alkylene;
or R$_5$ and X together with the atoms to which they are attached form a 6- or 7-membered ring, wherein said 6- or 7-membered ring contains a linking group —C(O)O— or —OC(O)—;
R$_7$ is hydrogen, methyl, —CH(R$_{17}$)(R$_{18}$), —C(O)O—R$_{18}$, or —OC(O)—R$_{18}$; wherein
R$_{17}$ is hydrogen or C$_{1-6}$ alkyl;
R$_{18}$ is hydrogen, C$_{1-6}$ alkyl, —CH(R$_{19}$)(R$_{20}$), phenyl, naphthyl, C$_{3-6}$ cycloalkyl, norbornyl, adamantyl, a natural or unnatural amino acid or a peptide;
R$_{19}$ is hydrogen or C$_{1-6}$ alkyl;
R$_{20}$ is hydrogen, C$_{1-6}$ alkyl;
R$_8$ is —H or -C$_{1-6}$alkyl;
R$_9$ is hydrogen, C$_{1-6}$ alkyl, phenyl, naphthyl, C$_{3-6}$ cycloalkyl, norbornyl, adamantyl, a natural or unnatural amino acid or a peptide;
R$_{11}$ and R$_{12}$ are hydrogen, hydroxyl, C$_{1-6}$ alkyl, —OCH$_3$, —CF$_3$, NO$_2$, or either or both of R$_{11}$ and R$_{12}$ contain a reactive group on to which a linker and/or one or more of compound W can be added;
E is C$_1$-C$_6$alkylene;
G and G$_1$ are independently N or CR$_{16}$;
R$_{16}$ is hydrogen or methyl;
compound W is one or more amino acids, one or more sugars, polymeric ethers, C$_{1-6}$alkylene-phenyl—NH—C(O)—R$_{15}$, folic acid, α$_\nu$β$_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof; and
Z is independently one or more halo or nitro, or one or more counterions sufficient to balance the charge of the compound.

In an embodiment, R$_{11}$ and R$_{12}$ are independently —OH, —N$_3$, —COOH, —CONH$_2$, —CH═CH$_2$, —C≡CH, —(CH$_2$)$_{1-6}$—OH, —(CH$_2$)$_{1-6}$—N$_3$, —(CH$_2$)$_{1-6}$—COOH, —(CH$_2$)$_{1-6}$—CH═CH$_2$, —(CH$_2$)$_{1-6}$—C≡CH, —(CH$_2$)$_{0-1}$(—OCH$_2$CH$_2$)$_{1-6}$—OH, —(CH$_2$)$_{0-1}$(—OCH$_2$CH$_2$)$_{1-6}$—N$_3$, or —(CH$_2$)$_{0-1}$(—OCH$_2$CH$_2$)$_{1-6}$—COOH;

In an embodiment, R$_{11}$ and R$_{12}$ combined with the linker and compound W are —NH—R$_{13}$,

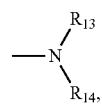

—O—R$_{13}$, —CH═CH—R$_{13}$, —C≡C—R$_{13}$,

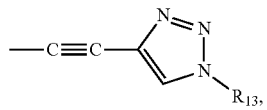

—N$_3$, —COOH, —COOR$_{14}$, —C(O)NH—R$_{13}$, —NHC(O)—R$_{13}$, —OC(O)NH—R$_{13}$, —OC(O)O—R$_{13}$, —(CH$_2$)$_{1-6}$—NH—R$_{13}$,

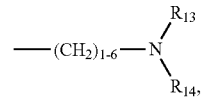

—(CH$_2$)$_{1-6}$—O—R$_{13}$, —(CH$_2$)$_{1-6}$—N$_3$, —(CH$_2$)$_{1-6}$—COOH, —(CH$_2$)$_{1-6}$—COOR$_{14}$ or —(CH$_2$)$_{1-6}$—CH═CH—R$_{13}$;

wherein R$_{13}$ and R$_{14}$ are independently selected from the group consisting of one or more amino acids, one or more sugars, polymeric ethers, PAMAM (Poly(amido amine)) Dendrimers such as carboxylate-modified PAMAM Dendrimers, PLGA (poly(lactic-co-glycolic acid)), -triazol-R$_{15}$, C$_{1-6}$alkylene-phenylene—NH—C(O)—R$_{15}$, folic acid, fatty acid, and polyunsaturated fatty acid (PUFA), α$_\nu$β$_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof;

wherein R$_{15}$ is a peptide; and
the benzene ring which is T is optionally present.

In an embodiment, the present invention relates to the compounds of Formula II, and pharmaceutically acceptable salts and solvates thereof:

Formula II

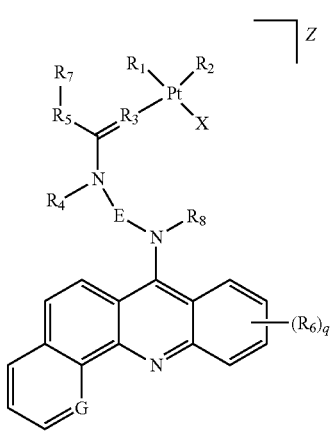

wherein X is halo, OC(O)R$_9$, nitrate or sulfate;

R$_1$ and R$_2$ are amino groups or together with the platinum atom to which they are attached, R$_1$ and R$_2$ form the ring —NH$_2$—(CH$_2$)$_v$—NH$_2$— wherein v is 1, 2, 3, or 4 or R$_1$ and R$_2$ together can be any of the following groups a-h;

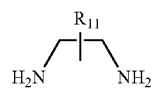
a

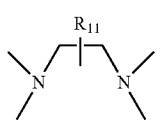
b

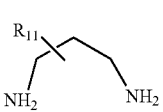
c

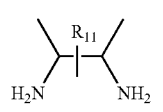
d

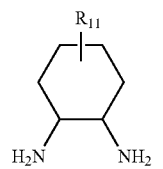
e

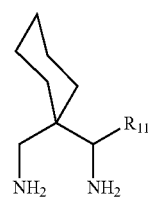
f

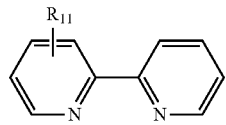
g

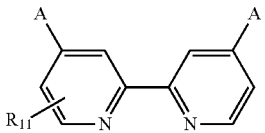
h wherein A is H, —CH$_3$, —OCH$_3$, CF$_3$ or NO$_2$;

R$_3$ is —N(R$_{26}$)—; wherein R$_{26}$ is hydrogen or C$_1$-C$_6$alkyl;

R$_4$ is hydrogen, C$_{1-6}$ alkyl, or CH$_2$—R$_{12}$;

R$_6$ is independently an amino, a nitro, —NHC(O)(R$_{10}$), —NHC(O)O(R$_{10}$), —C(O)NHR$_{10}$, —OC(O)NHR$_{10}$, or halo;

R$_{10}$ is hydrogen, C$_{1-6}$ alkyl, phenyl, naphthyl, C$_{3-6}$ cycloalkyl, norbornyl, or adamantyl;

q is 0, 1, or 2;

R$_5$ is a direct bond, —NH— or C$_1$-C$_6$alkylene;

or R$_5$ and X together with the atoms to which they are attached form a 6- or 7-membered ring, wherein said 6- or 7-membered ring contains a linking group —C(O)O— or —OC(O)—;

R$_7$ is hydrogen, methyl, —CH(R$_{17}$)(R$_{18}$), —C(O)O—R$_{18}$, or —OC(O)—R$_{18}$; wherein R$_{17}$ is hydrogen or C$_{1-6}$ alkyl;

R$_{18}$ is hydrogen, C$_{1-6}$ alkyl, —CH(R$_{19}$)(R$_{20}$), phenyl, naphthyl, C$_{3-6}$ cycloalkyl, norbornyl, adamantyl, a natural or unnatural amino acid or a peptide;

R$_{19}$ is hydrogen or C$_{1-6}$ alkyl;

R$_{20}$ is hydrogen, C$_{1-6}$ alkyl;

R$_8$ is —H or -C$_{1-6}$alkyl;

R$_9$ is hydrogen, C$_{1-6}$ alkyl, phenyl, naphthyl, C$_{3-6}$ cycloalkyl, norbornyl, adamantyl, a natural or unnatural amino acid or a peptide;

R$_{11}$ and R$_{12}$ are hydrogen, C$_{1-6}$ alkyl, or either or both of R$_{11}$ and R$_{12}$ contain a reactive group on to which a linker and/or one or more of compound W can be added;

E is C$_1$-C$_6$alkylene;

G is N or CR$_{16}$;

R$_{16}$ is hydrogen or methyl;

compound W is one or more amino acids, one or more sugars, polymeric ethers, C$_{1-6}$alkylene-phenyl—NH—C(O)—R$_{15}$, folic acid, α$_v$β$_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof; and Z is independently one or more halo or nitro, or one or more counterions sufficient to balance the charge of the compound.

In an embodiment, R$_{11}$ and R$_{12}$ are independently —OH, —N$_3$, —COOH, —CONH$_2$, —CH═CH$_2$, —C≡CH, —(CH$_2$)$_{1-6}$—OH, —(CH$_2$)$_{1-6}$—N$_3$, —(CH$_2$)$_{1-6}$—COOH, —(CH$_2$)$_{1-6}$—CH═CH$_2$, —(CH$_2$)$_{1-6}$—C≡CH, —(CH$_2$)$_{0-1}$(—OCH$_2$CH$_2$)$_{1-6}$—OH, —(CH$_2$)$_{0-1}$(—OCH$_2$CH$_2$)$_{1-6}$—N$_3$, or —(CH$_2$)$_{0-1}$(—OCH$_2$CH$_2$)$_{1-6}$—COOH;

In an embodiment, R$_{11}$ and R$_{12}$ combined with the linker and compound W are —NH—R$_{13}$,

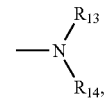

—O—$R_{13}$, —CH=CH—$R_{13}$, —C≡C—$R_{13}$,

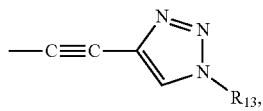

—$N_3$, —COOH, —COO$R_{14}$, —C(O)NH—$R_{13}$, —NHC(O)—$R_{13}$, —OC(O)NH—$R_{13}$, —OC(O)O—$R_{13}$, —(CH$_2$)$_{1-6}$—NH—$R_{13}$,

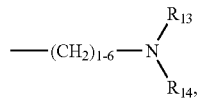

—(CH$_2$)$_{1-6}$—O—$R_{13}$, —(CH$_2$)$_{1-6}$—$N_3$, —(CH$_2$)$_{1-6}$—COOH, —(CH$_2$)$_{1-6}$—COO$R_{14}$ or —(CH$_2$)$_{1-6}$—CH=CH—$R_{13}$;

wherein $R_{13}$ and $R_{14}$ are independently selected from the group consisting of one or more amino acids, one or more sugars, polymeric ethers, PAMAM (Poly(amido amine)) Dendrimers such as carboxylate-modified PAMAM Dendrimers, PLGA (poly(lactic-co-glycolic acid)), -triazol-$R_{15}$, $C_{1-6}$alkylene-phenylene—NH—C(O)—$R_{15}$, folic acid, fatty acid, and polyunsaturated fatty acid (PUFA), $\alpha_v\beta_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof;

wherein $R_{15}$ is a peptide.

In an embodiment, the variables of formula I and/or II may be any of the follows: $R_3$ may be —N($R_{26}$)—, wherein $R_{26}$ is $C_{1-3}$alkyl or hydrogen. In a variation, Y may be —CH$_2$—. In a variation, $R_1$ and $R_2$ may be amino groups or together with the platinum atom to which $R_1$ and $R_2$ are attached are —NH$_2$—CH$_2$—NH$_2$—. In a variation, the counter ion Z comprises NO$_3$. In a further variation, $R_5$ may be —NH— or —CH$_2$—. In a further variation, $R_{26}$ may be hydrogen or methyl.

In an embodiment, the variables of formula I and/or II may be any of the follows: $R_6$ may be NO$_2$ or halo, or NO$_2$ or —F. E may be $C_{1-3}$alkylene or methylene or ethylene. $R_3$ may be NH or NCH$_3$. $R_5$ and $R_7$ together may be $C_{1-3}$alkyl or methyl or ethyl. $R_8$ may be H or CH$_3$. X may be chloro or fluoro. $R_5$ and $R_7$ may be amino groups. $R_4$ may be —H or —CH$_3$. G and $G_1$ may both be CH or G and $G_1$ may both be N. $R_{11}$ may be hydrogen or methyl.

In an embodiment, the present invention relates to the compounds shown below in Table I, and pharmaceutically acceptable salts and solvates thereof.

In an embodiment, the present invention relates to:
(i) new platinum-chromophore hybrid agents capable of producing nanomolar cytotoxicity in several aggressive NSCLC lines and possessing the ability to bind to non-classical DNA secondary structures, such as G-quadruplex DNA.
(ii) chemical compounds containing favorable geometric and electrostatic properties capable of overcoming limitations of current platinum-based chemotherapy, mainly systemic toxicity.
(iii) structurally new and previously undisclosed platinum-chromophore hybrid structures containing extended aromatic chromophores, including but not limited to, P1-B1 and P1-B2, have been designed and synthesized.
(iv) compounds that display a p53 independent cell-kill mechanism, which differs from the p53-dependent cell-kill mechanism demonstrated by other prototypes and cisplatin, P3-A1.
(v) Selective recognition of G-quadruplex DNA, as displayed by induced circular dichroism (ICD), with P1-B1 and P1-B2, which was not previously displayed by the prototype, P1-A1.

In an embodiment, the present invention relates to pre-screen involving a plurality of derivatives of platinum-benzacridine hybrid agents that have been tested in vitro in two NSCLC lines. These agents have been tested in structure-activity relationship studies comparing their cytotoxicity to the previously described platinum-acridine hybrid agents (P1-A1). Compound P1-B1 maintained nanomolar cytotoxicity after 72 hour incubations in extremely aggressive NSCLC models.

The Platinum-based compounds of the present invention may also be used against genitourinary (bladder, ovaries, testes) cancers and carcinomas of the head and neck, as well as colon cancers. Although the compounds of the present invention may also show promise against these various cancers and carcinomas, the compounds of the present invention show an altered spectrum of activity compared to previous drugs used against these various cancers and carcinomas, the compounds of the present invention also show excellent activity in cancers insensitive to the clinical platinums of the prior art.

In an embodiment, the present invention discloses methods of treating cancer in an individual in need thereof by the use of a compound of Formula I or II.

In a variation, the compounds of the present invention can be used for treating diseases of abnormal cell growth and/or dysregulated apoptosis, such as cancer, mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia , esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumors, primary or secondary brain tumors, Hodgkin's disease, chronic or acute leukemias, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non-Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblastoma, or a combination thereof.

In a variation, the compounds of the present invention can be used in the treatment of non-small cell lung cancer, pancreatic cancer, breast cancer, and ovarian cancer. Alternatively, the compounds of the present invention can be used in the treatment of non-small cell lung cancer, pancreatic, and ovarian cancer.

In an embodiment, the compounds of the present invention also have potential applications as antiviral and anti-Alzheimer's drugs.

Thus, it is contemplated that the compounds, compositions and methods of the present invention may be useful for first- and/or second-line treatment option for cancers that are inherently resistant, or, have become resistant to clinical therapies, especially classical platinum drugs. The compounds of the present invention may provide an avenue to solve the urgent need for mechanistically novel drugs for the life-prolonging/curative treatment of NSCLC.

Salable: a drug preparation (reconstitutable powder, saline solution)

Computational Studies of Design Elements

Computational studies on both the chromophores and platinums were conducted to determine suitable modules for the combinatorial library. Chromophores with 2-5 aromatic rings and 1-2 protonable endocyclic nitrogen atoms (Chart 1) were studied to determine their free energy of protonation (Table 1). Since the goal was to decrease the overall charge of the final platinum-chromophore hybrid, chromphores possessing a more-positive free energy than 9-methylaminoacridine (2) were considered "hits". From the list of available "hits", unsubstituted and nitro-subsituted benz[c] acridines, and quinoline were chosen as modules in the combinatorial library due to feasibility of synthesis. These chromophores were hypothesized to have a lower pKa than the acridine chromphore.

The below chromophores were used in computational screening with the protonation sites studied highlighted.

Thus, in an embodiment, the present invention relates to the chromophores in chart 1 that can be added to a platinum containing moiety that makes up compounds, pharmaceutically acceptable salts and solvates. In one embodiment, the present invention relates to the chromophores in chart 1 that can have a platinum containing moiety added to it that makes up the compounds, pharmaceutically acceptable salts and solvates that are represented by chromophores 3, 3a-d, 4, 4a-b, 5, 5a-b, and 6.

Chart 1

1
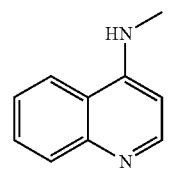

2
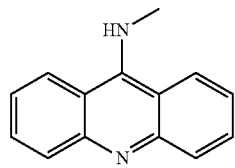

3: $R_1 = R_2 = H$
3a: $R_1 = F, R_2 = H$
3b: $R_1 = H, R_2 = F$
3c: $R_1 = NO_2, R_2 = H$
3d: $R_1 = H, R_2 = NO_2$

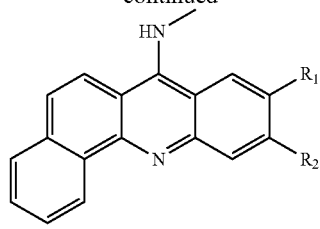

4: $R_1 = R_2 = H$
4a: $R_1 = F, R_2 = H$
4b: $R_1 = H, R_2 = F$

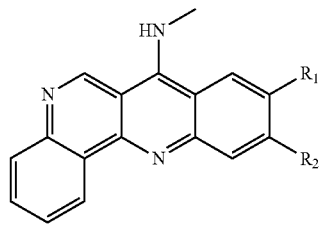

5: $R_1 = R_2 = H$
5a: $R_1 = F, R_2 = H$
5b: $R_1 = H, R_2 = F$

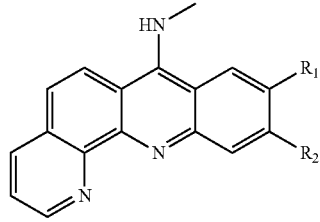

6
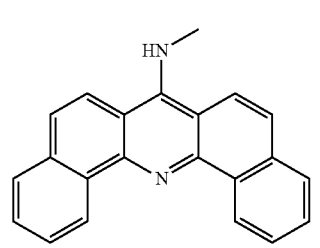

Table 1 shows the free energies of protonation of each chromophore with DFT optimized geometries in a self-consistent reaction field with the dielectric constant of water.

TABLE 1

| Chromophore | $\Delta G_{protonation}$ kJ/mol |
| --- | --- |
| 3d | −139.94 |
| 3c | −140.86 |
| 4a | −142.93 |
| 4b | −143.08 |
| 6 | −145.80 |
| 4 | −149.74 |
| 3a | −151.40 |
| 3b | −154.57 |
| 3 | −158.40 |
| 1 | −170.06 |
| 2 | −174.02 |

TABLE 1-continued

| Chromophore | $\Delta G_{protonation}$ kJ/mol |
|---|---|
| 5a | −177.83 |
| 5b | −180.58 |
| 5 | −184.44 |

The platinum modules were evaluated by determining the kinetic and thermodynamic properties associated with both aquation and nucleobase binding with variable non-leaving amine groups (Chart S1).

Chart S1

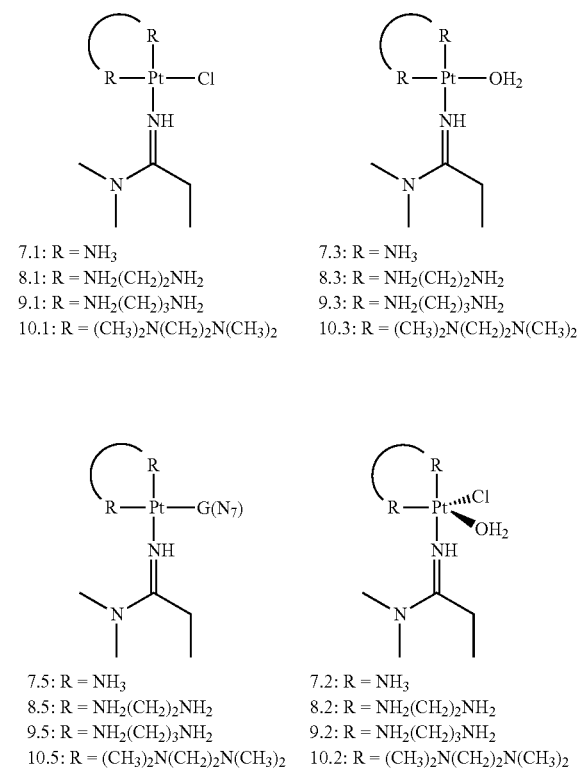

7.1: R = NH$_3$
8.1: R = NH$_2$(CH$_2$)$_2$NH$_2$
9.1: R = NH$_2$(CH$_2$)$_3$NH$_2$
10.1: R = (CH$_3$)$_2$N(CH$_2$)$_2$N(CH$_3$)$_2$ 7.3: R = NH$_3$
8.3: R = NH$_2$(CH$_2$)$_2$NH$_2$
9.3: R = NH$_2$(CH$_2$)$_3$NH$_2$
10.3: R = (CH$_3$)$_2$N(CH$_2$)$_2$N(CH$_3$)$_2$ 7.5: R = NH$_3$
8.5: R = NH$_2$(CH$_2$)$_2$NH$_2$
9.5: R = NH$_2$(CH$_2$)$_3$NH$_2$
10.5: R = (CH$_3$)$_2$N(CH$_2$)$_2$N(CH$_3$)$_2$ 7.2: R = NH$_3$
8.2: R = NH$_2$(CH$_2$)$_2$NH$_2$
9.2: R = NH$_2$(CH$_2$)$_3$NH$_2$
10.2: R = (CH$_3$)$_2$N(CH$_2$)$_2$N(CH$_3$)$_2$

-continued

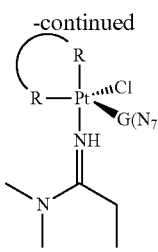

7.4: R = NH$_3$
8.4: R = NH$_2$(CH$_2$)$_2$NH$_2$
9.4: R = NH$_2$(CH$_2$)$_3$NH$_2$
10.4: R = (CH$_3$)$_2$N(CH$_2$)$_2$N(CH$_3$)$_2$

Figure 3:
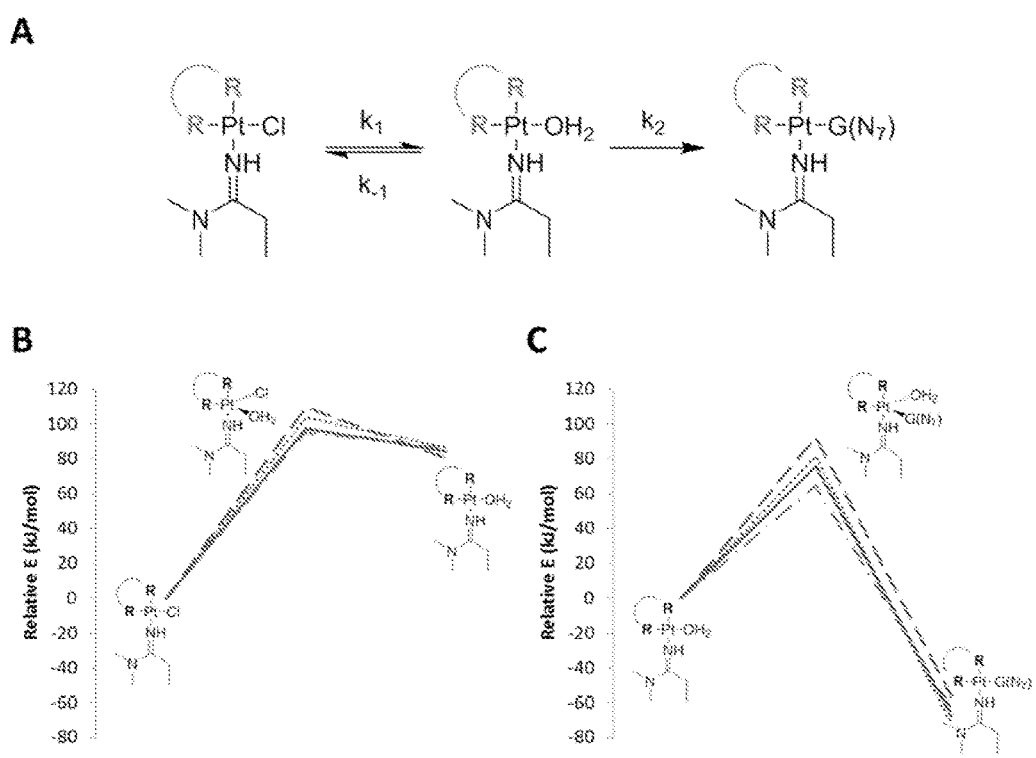
FIG. 3 shows the effects of non-leaving group on platinum nucleobase binding. (A) The overall reaction of nucleobase binding was broken down into its kinetic and thermodynamic components of (B) reversible aquation and (C) irreversible guanine binding. Non-leaving groups are ammonia (green dotted line), ethylenediamine (red solid line), propylenediamine (yellow dash dot line), and tetramethylethylenediamine (blue dashed line).

To decrease non-specific binding with duplex DNA, a slow aquation and nucleobase binding was preferable, so that the chromophore directs subcellular accumulation. Due to this hypothesis, it was determined by the energy diagrams of all platinum models (FIG. 3) that the $N^1,N^1,N^2,N^2$-tetramethylethane-1,2-diamine non-leaving group would have the slowest overall aquation and nucleobase binding, whereas the 1,3-diaminopropane non-leaving group was the fastest in both processes. Due to synthetic feasibility, all four platinum models studies were used as modules in the combinatorial library.

Synthesis of Chromophores

The quinoline and acridine chromophores with the appropriate diamine linkers were synthesized from their phenoxy precursors similar to those previously described in literature.[3] The benz[c]acridine derivatives (Scheme 1) were synthesized by utilizing the appropriate substituted o-chlorobenzoic acid with 1-napthylamine via an Ullman condensation. This product was then cyclized by phosphorus oxychloride. Due to activation of the 7-position of the nitrobenz[c]acridines, the amine could be added using the 7-chloro or the 7-phenoxy intermediate. In the case of the unsubstitued benz[c]acridine, however, reactivity was significantly decreased which only allowed for substitution of a boc-protected amine linker to the 7-phenoxy precursor. When unprotected amine linkers were used, substitution occurred at both the primary and secondary amines.

Scheme 1 Shows the Synthesis of Various Benz[c]acridine Chromophores

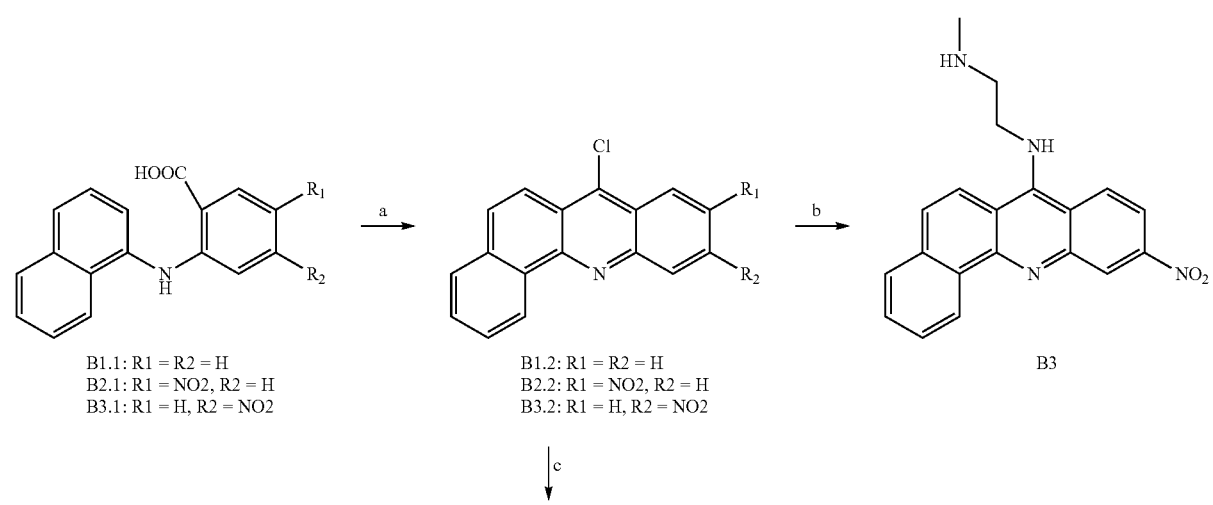

B1.1: R1 = R2 = H
B2.1: R1 = NO2, R2 = H
B3.1: R1 = H, R2 = NO2

B1.2: R1 = R2 = H
B2.2: R1 = NO2, R2 = H
B3.2: R1 = H, R2 = NO2

B3

-continued

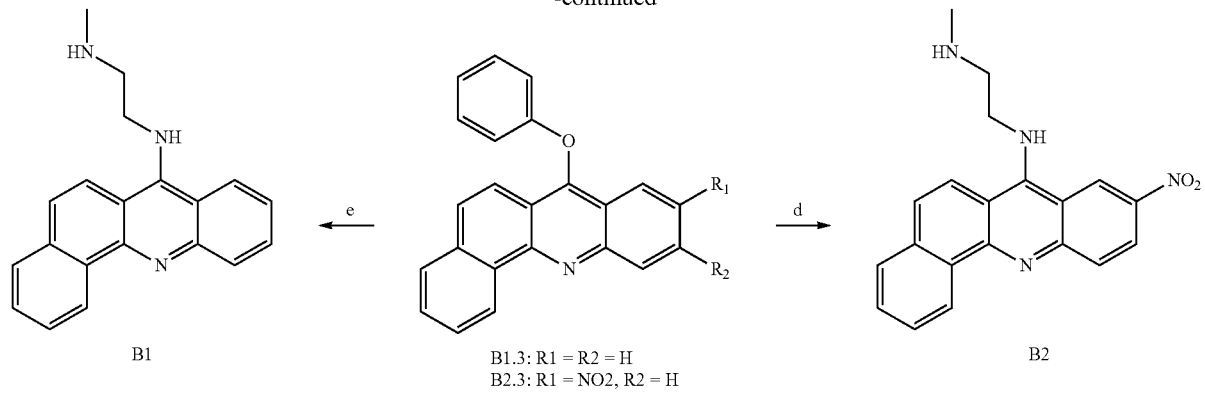

Scheme 1 Reagents and Conditions: (a) POCl$_3$, 80° c, (b) (1) N-methylethylenediamine, dioxane, reflux, (2) 2M NH$_4$OH (c) NaOH, phenol, 120C, (d) (1) N-methylethylenediamine, dioxane, reflux, (2) 2M NH$_4$OH, (e) (1) tert-butyl (2-aminoethyl)(methyl)carbamate, triethylamine, dioxane, reflux, (2) HCl/HAc, (3) 2M NaOH Scheme 2 shows another exemplary scheme for making other compounds of the present invention. Please note that the platinum-containing moiety can be modified to insert whatever desired moiety is wanted. It should be understood that other methods of making the compounds of the present invention are contemplated and within the scope of the present invention.

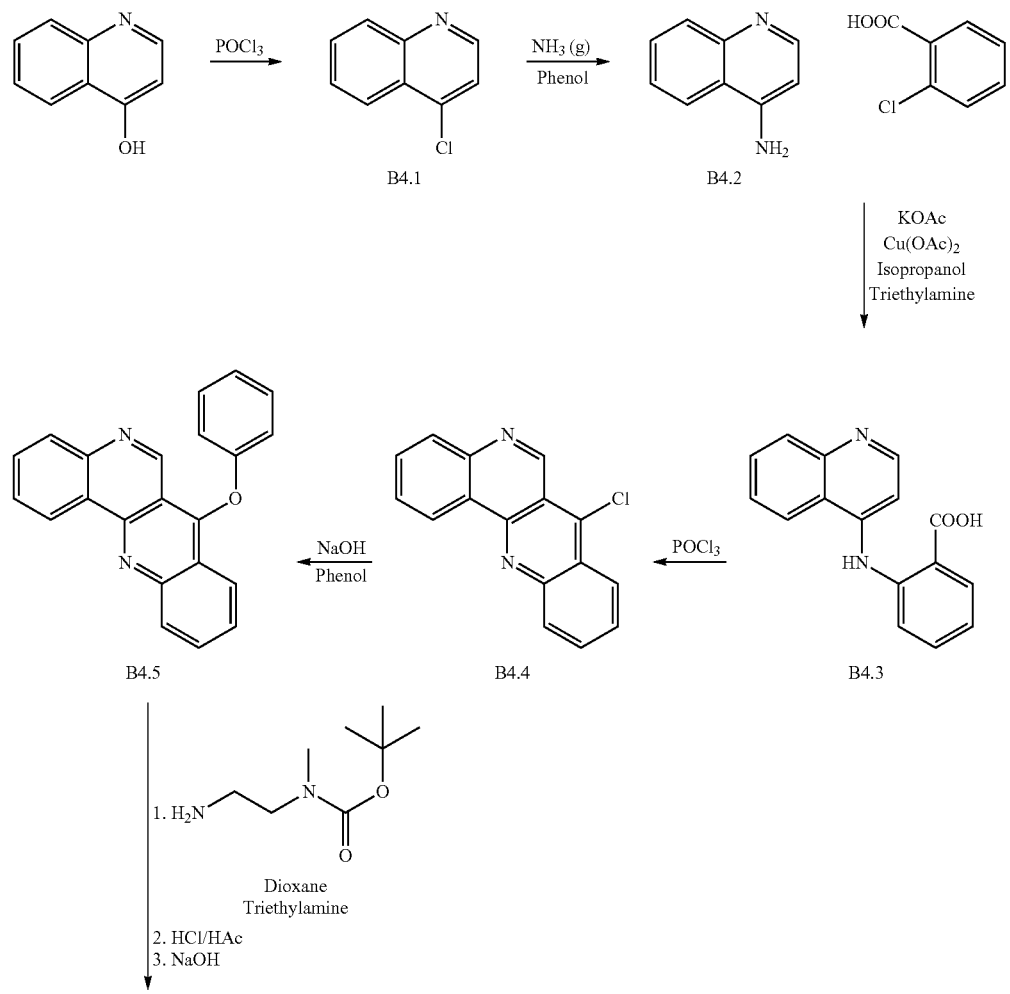

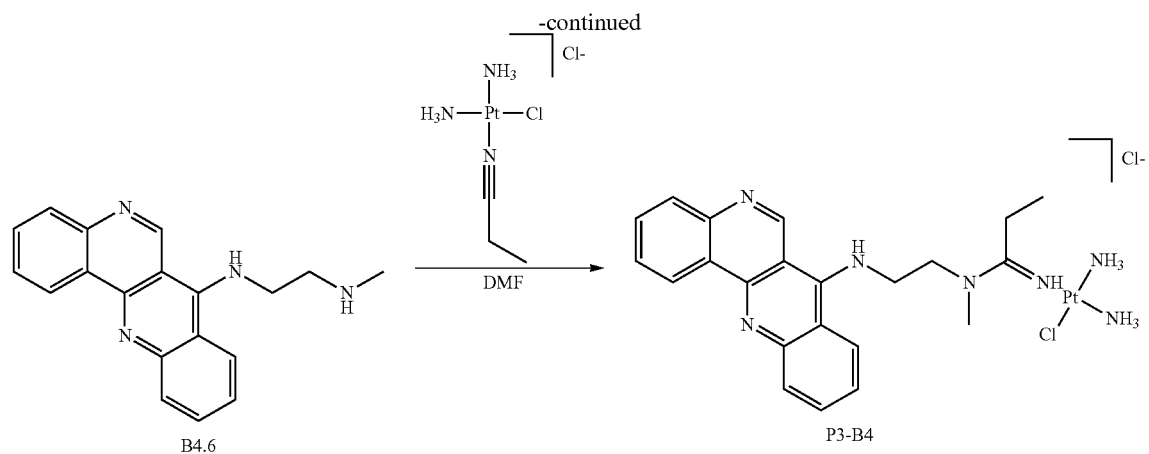

Scheme 3 shows another synthetic scheme to make additional compounds of the present invention. As is the case with scheme 2, please note that the platinum-containing moiety can be modified to insert whatever desired moiety is wanted. It should also be understood that other methods of making the compounds of the present invention are contemplated and within the scope of the present invention.

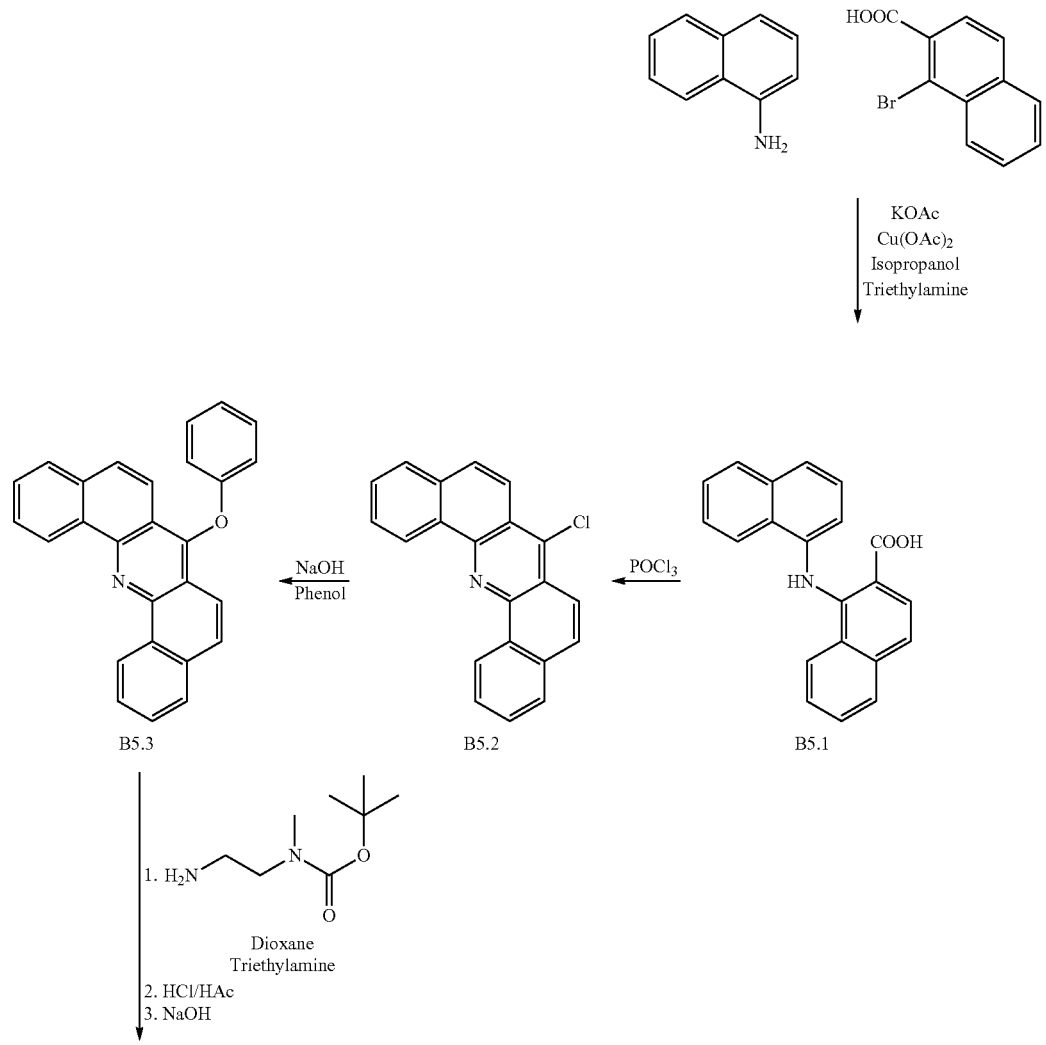

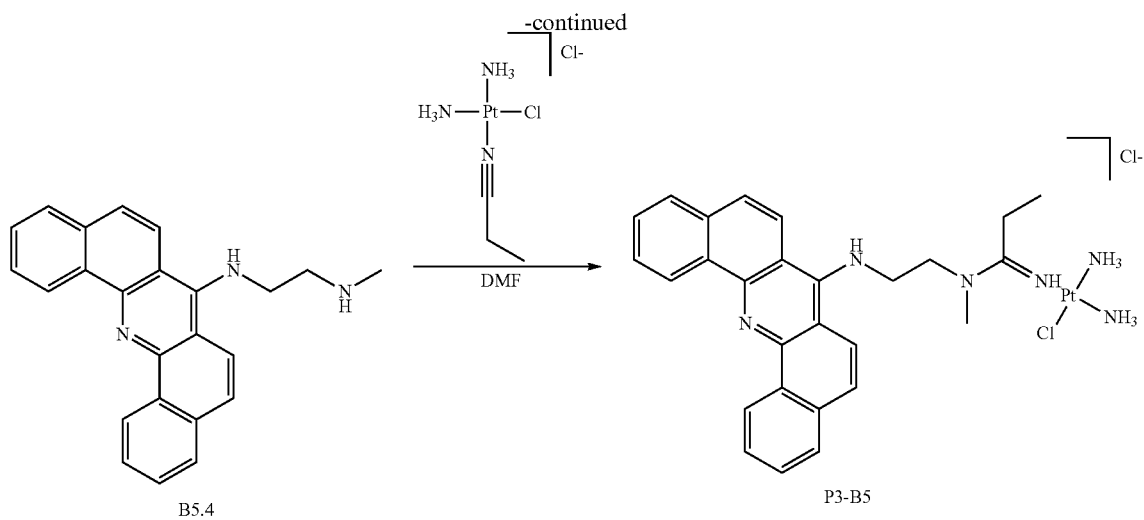

Scheme 4 shows another synthetic scheme to make additional chromophores that can be used to make the compounds of the present invention. As is the case with schemes 2 and 3, please note that the platinum-containing moiety can be modified to insert whatever desired moiety is wanted. It should also be understood that other methods of making the compounds of the present invention are contemplated and within the scope of the present invention.

Modular Library Assembly and Pre-Screening

After synthesizing the chromophore and platinum modules (Chart 2), stock solutions were made in anhydrous DMF and combined (FIG. 1) to create twenty unique Pt-chromophore hybrid drugs.

Chart 2 Shows Platinum (P) and Chromophore (Q, A, B) Modules for the Combinatorial Library

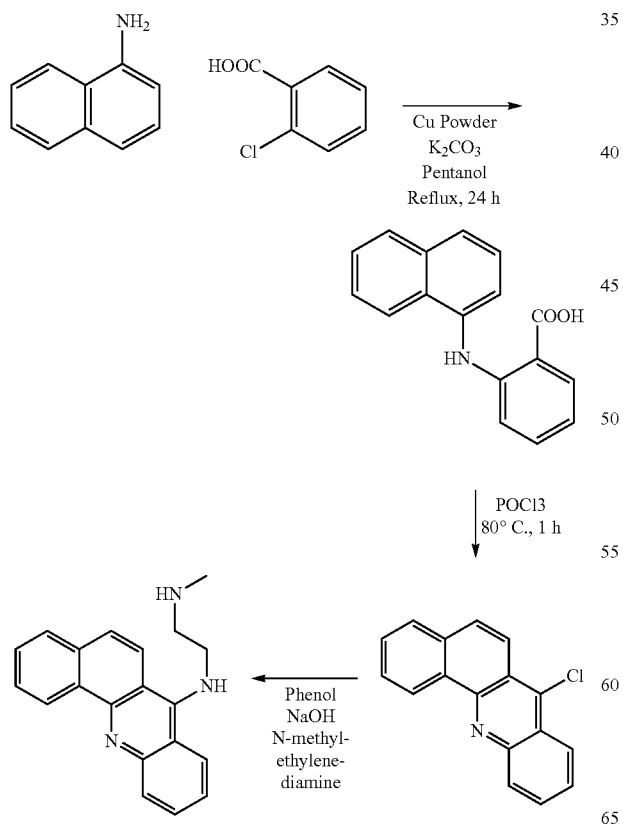

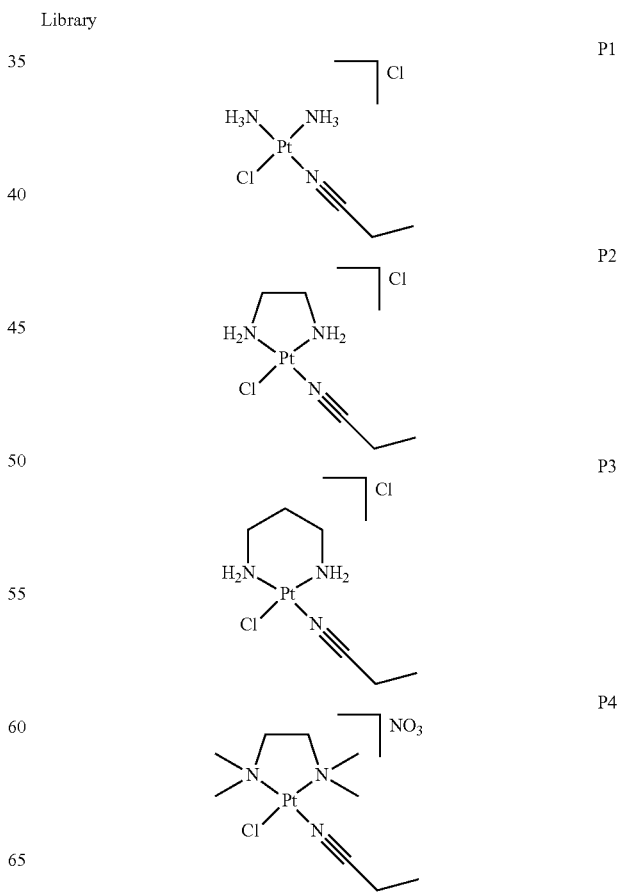

-continued

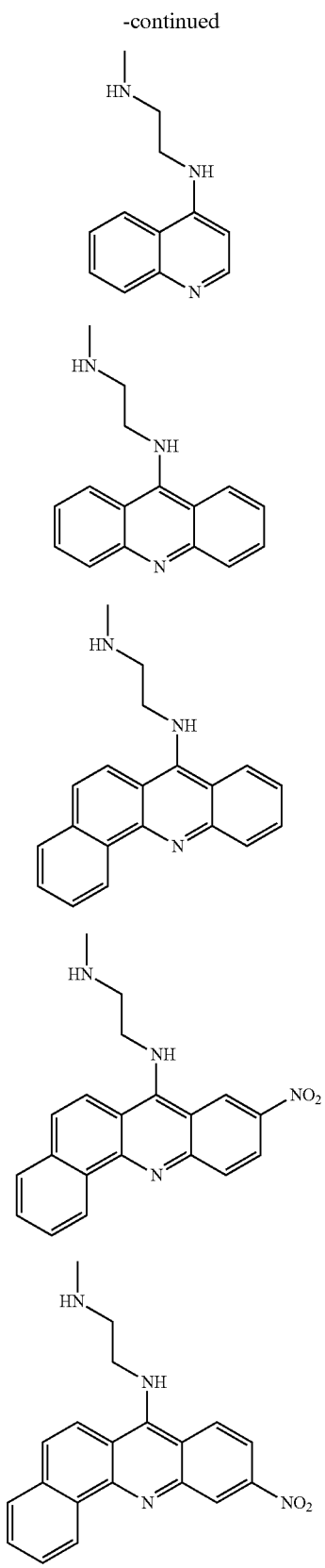

Q1
A1
B1
B2
B3

Figure 2:
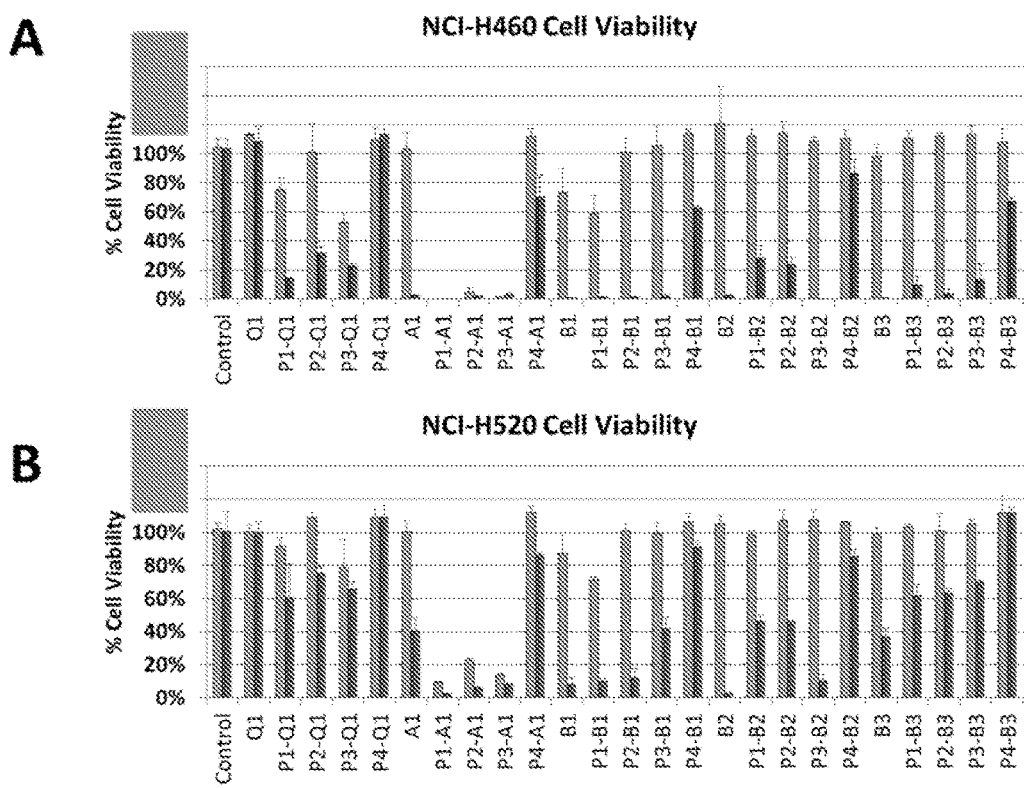
FIG. 2 shows the biological activity profiles of 20 compounds based on the cell viability of the drug-treated cells compared to the untreated controls. Compounds were tested in (A) NCI-H460 cells and (B) NCI-H520 cells incubated at both 1 μM drug (shaded bars) and 10 μM drug (solid bars) concentrations. Error bars represent the standard deviation of three separate wells.

The crude reaction mixtures were diluted to the appropriate concentrations with media and tested for cytotoxicity in NCI-H522 (squamous cell) and NCI-H460 (large cell) non-small-cell lung carcinomas (FIG. 2). As expected, the previously described Pt-acridine hybrid agents[4] (A1) displayed the greatest cell-kill ability when compared to the quinoline and benz[c]acridine chromophores. There were, however, two chromphores that demonstrated similar cytoxocity in both cell lines, which were B1 and B2. The platinum moiety P1 was chosen as a compromise between in vitro cytotoxicity and predicted kinetic properties from the computational studies. Even though P4 displayed the slowest, and most favorable, aquation and platination from computational studies, it seems that it is too slow to have acceptable cell-kill ability in vitro.

Determination of Platinum Content Associated with Nucleic Acids in NCI-H460 Cells To determine the platinum content of nucleic acid material, DNA and RNA was extracted and purified from cells using the Qiagen AllPrep DNA/RNA Mini Kit (Qiagen, Alameda, Calif., USA). $1.5 \times 10^6$ exponentially-growing NCI-H460 cells were seeded into 60-mm cell culture dishes with 2 mL of media and were allowed to attach for 24 hours. Cells were incubated in the presence of 1 μM P1-A1 or P1-B1 at 37° C. for various time intervals. Incubations were performed in triplicate for each incubation condition/time point. To quench the incubations, cells were washed three times in cold PBS. The cells were harvested via trypsinization and removed from the dishes with successive washes of cold PBS. Cell suspensions were centrifuged at 1500 rpm for 5min at 4° C. The cell pellet was re-suspended in 5 mL of cold PBS and centrifuged at 1500 rpm for 5 min at 4° C. The supernatant was removed and the DNA/RNA was extracted from the pellet according to the protocol provided by the manufacturer. The concentration and purity of each sample was determined spectrophotometrically (triplicate readings at 260 and 280 nm).

Platinum content was determined by ICP-MS.

Figure 4:
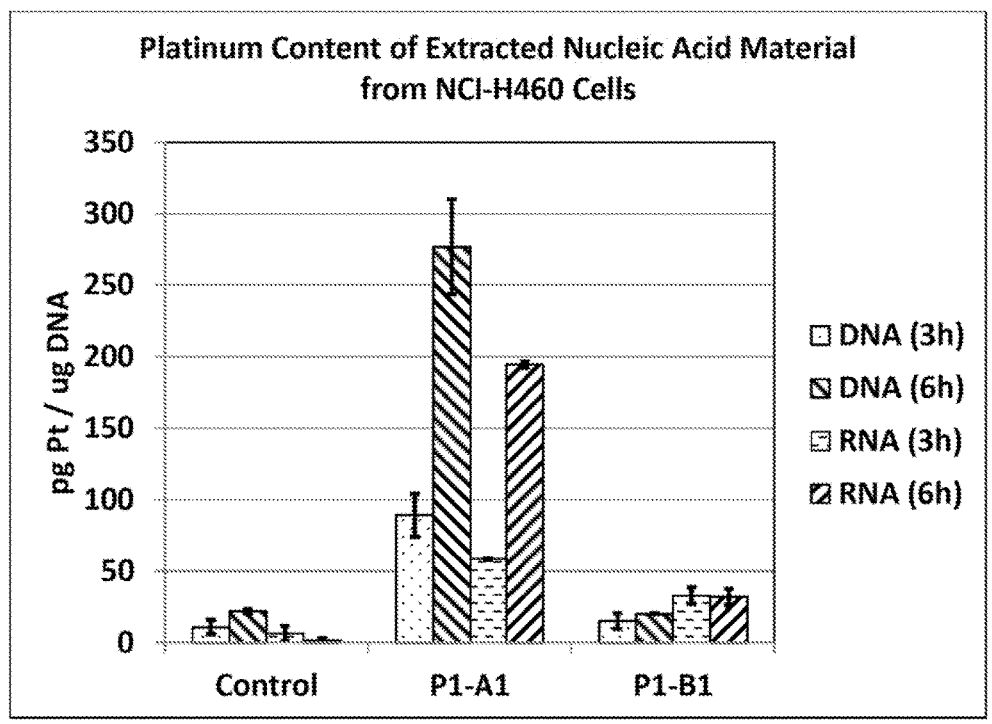
FIG. 4 shows platinum amounts extracted from DNA and RNA from NCI-H460 cells.

The results of these experiments are shown in FIG. 4. The platinum level observed in the DNA of P1-B1 treated cells was not statistically significant from that found in the control cells ($p>0.05$) at both time points. The platinum level observed in the RNA of P1-B1 at 3 h was statistically significant ($p<0.05$). This suggests that the addition of a benzene ring to form a benzacridine chromophore shifts the target of this platinum-hybrid agent away from DNA, potentially to RNA.

P1-B1, a platinum-benzacridine hybrid agent, retains the ability to inhibit RNA transcription and induce submicromolar cytotoxicity in aggressive cancer cell lines similar to the prototype P1-A1. P1-B1 retains these desirable features without causing the extensive DNA damage observed for the acridine-based prototypes, as well as platinum-based chemotherapies in the clinic. This suggests the ability to overcome the potentially dose-limiting genotoxicity caused by platinum-based chemotherapies and suggests a more selective targeting mechanism for cancer cell kill.

Re-Synthesis and Physicochemical Characterization of Target Compounds

After thorough assessment of the cytotoxicity results of the combinatorial library, it was determined that P1-A1 (control), P1-B1, and P1-B2 would be the best Pt-chromophore hybrid drugs to resynthesize and test in vivo to determine structure-activity relationships. These three drugs contain the same ammonia non-leaving amine group on the platinum and only differ in the chromophore size and substituents. The pKa of the three Pt-chromophore hybrid agents (Chart 3) agreed with the computational results, which indicated that the pKa of P1-B2 would be the lowest and P1-A1 would be the highest.

Chart 3 Shows Final Platinum Drugs with pKa Values

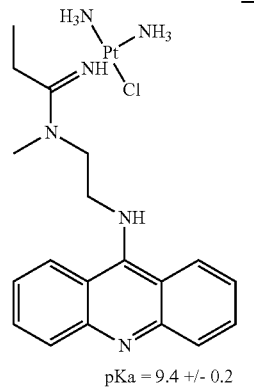

P1-A1 pKa = 9.4 +/- 0.2

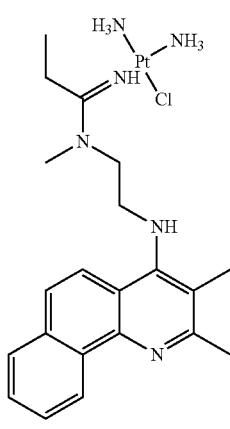

P1-B1 pKa = 7.6 +/- 0.3

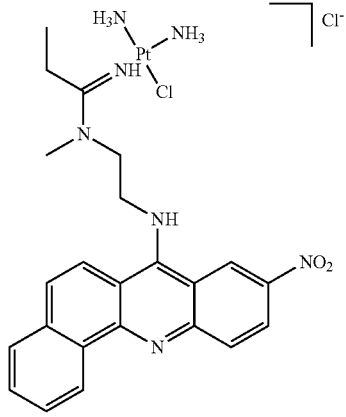

P1-B2 pKa = 4.9 +/- 0.6

Cell Culture Studies

After successful synthesis and purification of P1-A1, P1-B1, and P1-B2 was completed, each drug was tested for its cell-kill ability in five non-small-cell lung cancer cell lines (Table 2). The chromophore modules alone were tested in NCI-H460 and NCI-H520 cells and demonstrated that the benz[c]acridine chromophores were more cytotoxic than the acridine chromophore, with the unsubstitued benz[c]acridine (B1) resulting in the greatest cytotoxicity, which displayed an $IC_{50}$ value in the sub-micromolar range in NCI-H460 cells after a 72 h incubation.

When observing the structure-activity relationship of the platinum hybrid agents, it is important to note the increased cytotoxicity upon addition of the platinum module. In the case of P1-A1 and P1-B1, the platinum drugs performed significantly better than the chromphore alone. Also, P1-A1 displays significantly increased cytotoxicity in cell lines containing wildtype p53 (NCI-H460 and A549) versus cell lines containing mutant p53 (NCI-H520, NCI-H522, and NCIH1435). This trend, however, is not observed for P1-B1, which consistently displays $IC_{50}$ values around 100-500 nanomolar, except for in the case of NCI-H1435, which is an extremely repair-proficient cell line.[28] This data would suggest that P1-A1 and P1-B1 accomplish cell-kill via different mechanisms from each other.

Table 2 shows $IC_{50}$ values from the SAR study

| | $IC_{50}$ (µM) ± SD[a] | | | | |
|---|---|---|---|---|---|
| Compound | NCI-H460 | NCI-H520 | NCI-H522 | NCI-H1435 | A549 |
| A1 | 2.7 ± 0.1 | 4.4 ± 0.3 | b | b | b |
| B1 | 0.9 ± 0.1 | 1.8 ± 0.1 | b | b | b |
| B2 | 2.08 ± 0.04 | 3.35 ± 0.08 | b | b | b |
| P1-A1 | 0.00520 ± 0.00006 | 0.043 ± 0.004 | 0.0100 ± 0.0007 | 0.84 ± 0.07 | 0.0065 ± 0.0002 |
| P1-B1 | 0.24 ± 0.01 | 0.516 ± 0.009 | 0.12 ± 0.02 | 1.479 ± 0.009 | 0.32 ± 0.06 |
| P1-B2 | 2.4 ± 0.5 | 2.2 ± 0.1 | 3.62 ± 0.08 | 11.0 ± 0.2 | 12.4 ± 0.9 |

[a]Concentration of compound that reduces cell viability by 50%, determined at 72 h of drug incubation using the MTS (3-(4,5-dimethylthiazol-2-yl)-5-(3-carboxymethoxyphenyl)-2-(4-sulfophenyl)-2H-tetrazolium) assay. Values are means of duplicate experiments ± the standard deviation.
[b]Compound not tested in this cell line.

[a]Concentration of compound that reduces cell viability by 50%, determined at 72 h of drug incubation using the MTS (3-(4,5-dimethylthiazol-2-yl)-5-(3-carboxymethoxyphenyl)-2-(4-sulfophenyl)-2H-tetrazolium) assay. Values are means of duplicate experiments±the standard deviation.
[b]Compound not tested in this cell line.

Table 3 shows the various 4-ringed chromophores that can be made by using the starting materials that are present at the top and the left hand side of table 3 using the synthetic methods (or appropriate modifications thereof) of the synthetic methods that are present in the various schemes presented herein.

TABLE 3
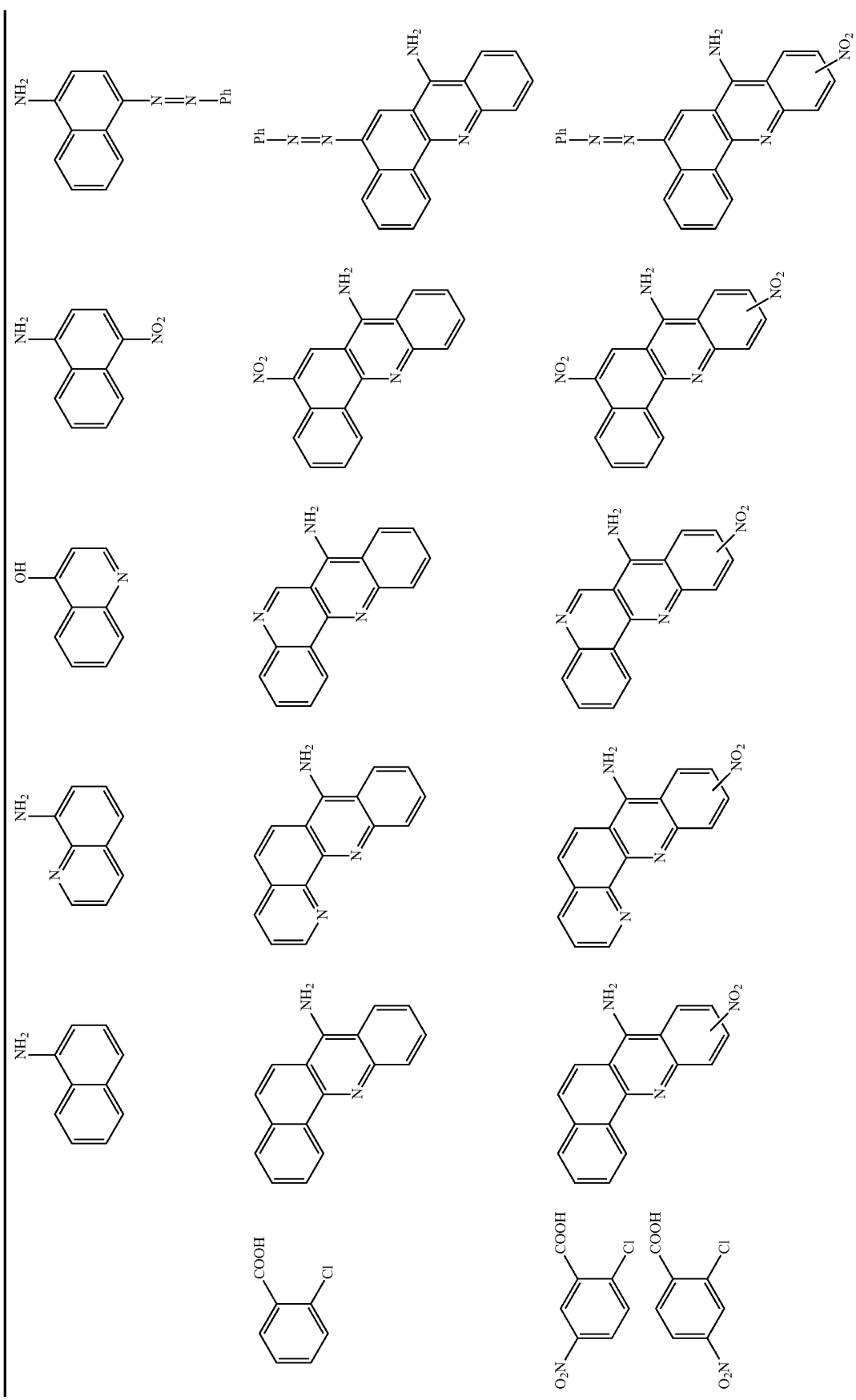

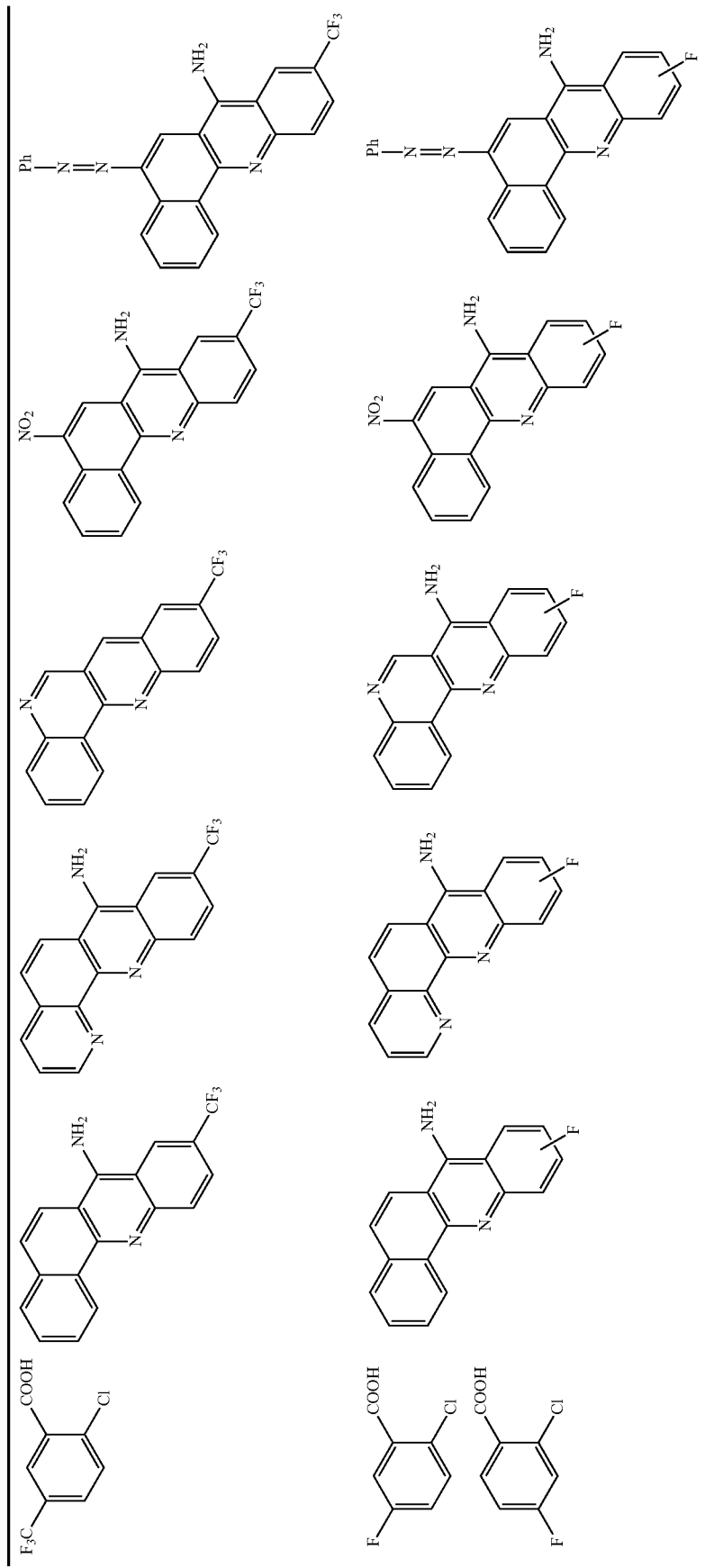

EXPERIMENTAL SECTION

Reagents and Instrumentation.

All reagents were used as obtained from commercial sources without further purification unless indicated otherwise. 1H NMR spectra of the target compounds and intermediates were recorded on a Bruker Advance 300 or a Bruker DRX-500 instrument operating at 300 or 500 MHz, respectively. 13C{1H}NMR spectra were recorded on a Bruker Advance 300 or a Bruker DRX-500 instrument operating at 75 or 125.8 MHz, respectively. Chemical shifts ($\delta$) are given in parts per million (ppm) relative to the internal standard tetramethylsilane (TMS). In-line LC-ESI-MS (High-performance Liquid-chromatrography electrospray-ionization mass spectrometry) analyses were performed on an Agilent 1100 LC/MSD ion trap mass spectrometer equipped with an electrospray ionization source. High-resolution mass spectrometry (HRMS) was performed on a Thermo Scientific LTQ Orbitrap XL equipped with an electrospray ionization source. All NMR and LCMS spectra were processed using the MestReNova Suite version 8.1.2 equipped with MS plugins. HRMS data was processed with Xcalibur 2.1 (Thermo Scientific). For the preparation of biological buffers, biochemical grade chemicals (Fisher/Acros) were used. HPLC grade solvents were used for all HPLC and mass spectrometry experiments. All reagents were used as obtained from commercial sources without further purification unless indicated otherwise. Stock solutions of platinum complexes in DMF (DMSO for P1-B2) were stored at −20° C. and thawed immediately before use.

Computational Studies.

All chromophore models were built using the Gaussview5 program.30 The optimization and single-point energy calculations were performed with the Gaussian 09 (G09) software package. All geometries were fully optimized in the gas phase at the gradient-corrected DFT level using the spin-unrestricted B3LYP functional and the 6-311G** basis set. Vibrational frequencies were used to confirm that the optimized structures had converged to their local minima and the equilibrium structures contained no imaginary frequencies. Single-point energy calculations were performed using the self-consistent reaction field (SCRF) approach to apply a constant dielectric constant of $\varepsilon$=78.3553 for water. All platinum models used for kinetic/thermodynamic studies were built, optimized, and calculated according to previously published procedure.7

Combinatorial Library.

Stock solutions of the chromophores (Q1, A1, B1, B2, B3) and the platinum-nitrile complexes (P1, P2, P3, P4) were made in dry DMF at a concentration of 300 mM. 200 µL aliquots of the chromophore stock solutions were added to 0.6 mL micro-centrifuge tubes and cooled to −20° C. The platinum-nitrile stock solutions/suspensions were homogenized by pipetting and added directly to the cooled chromophore solutions in 20 µL aliquots. The 1:1 mixtures were incubated at 4° C. for one week in a shaker. After 1 week, aliquots were taken from each sample and serial diluted to result in a 15 µM solution in methanol and 0.1% (v/v) formic acid. In-line LC-ESI-MS was used to determine the percent conversion for each micro-scale reaction using a 2.1×30 mm Rapid Resolution ZORBAX StableBond C-18 (3.5 µm) column, which was maintained at 40° C. The LC-ESI-MS was performed on an Agilent 1100LC/MSD ion trap mass spectrometer with an autosampler thermostatted at 4° C. at the appropriate separation and ionization conditions for each sample.

N1-methyl-N2-(quinolin-4-yl)ethane-1,2-diamine (Q1).

A solution of Q1.1 (503.6 mg, 2.277 mmol, 1 eq), tert-butyl (2-aminoethyl)(methyl)carbamate (773.3 mg, 4.434 mmol, 2 eq), and freshly distilled triethylamine (1 mL) in anhydrous dioxane (1 mL) was stirred at reflux for 72 h. The dioxane was removed by rotary evaporation and the remaining residue was stirred overnight in 4M HCl. Solution was basified with sodium hydroxide and extracted with chloroform. The chloroform layer was washed with brine and 2M NaOH before drying over sodium sulfate and activated carbon. The chloroform layer was filtered over celite, and the filtrate was evaporated and dried to yield a pure light yellow oil (273.3 mg, 60%, ≥95% by LC-ESI-MS). 1H NMR (300 MHz, DMSO-d6) $\delta$ 8.38 (d, J=5.3 Hz, 1H), 8.29-8.11 (m, 1H), 7.90-7.71 (m, 1H), 7.59 (ddd, J=8.3, 6.7, 1.4 Hz, 1H), 7.50-7.32 (m, 1H), 7.04 (s, 1H), 6.47 (d, J=5.4 Hz, 1H), 3.35 (t, J=6.5 Hz, 2H), 2.79 (t, J=6.4 Hz, 2H), 2.34 (s, 3H). 13C NMR (75 MHz, DMSO-d6) $\delta$ 150.58, 149.85, 148.20, 128.92, 128.55, 123.64, 121.51, 118.74, 98.10, 49.36, 41.95, 35.75. UV-Vis (BPES Buffer, pH=7.2 with 1% SDS): $\lambda$max 339, $\varepsilon$=13,008 M−1 cm−1.

N1-(benzo[c]acridin-7-yl)-N2-methylethane-1,2-diamine (B1).

A solution of B1.3 (917.8 mg, 2.856 mmol, 1 eq), tert-butyl (2-aminoethyl)(methyl)carbamate (777.6 mg, 4.463 mmol, 1.6 eq), anhydrous triethylamine (400 µL, 2.868 mmol, 1 eq) in 2 mL anhydrous dioxane was stirred at reflux for 5 days. The solvent was removed by rotary evaporation and the remaining residue stirred overnight in 4 mL of a 3:1 mixture of concentrated glacial acetic acid and concentrated hydrochloric acid. The acid was removed by rotary evaporation and the residue was neutralized with 2M NaOH. The yellow precipitate was extracted into chloroform and washed with brine and 2M NaOH. The chloroform layer was dried over sodium sulfate and activated carbon and filtered over celite. The chloroform was removed by rotary evaporation to yield a pure brown oil, which was dried in vacuo (778 mg, 90%, ≥95% by LC-ESI-MS). 1H NMR (300 MHz, Chloroform-d) $\delta$ 9.54-9.41 (m, 1H), 8.32-8.18 (m, 2H), 8.01 (d, J=9.4 Hz, 1H), 7.87-7.53 (m, 5H), 7.47 (ddd, J=8.3, 6.7, 1.3 Hz, 1H), 6.05 (s, 1H), 3.84-3.73 (m, 2H), 2.94-2.84 (m, 2H), 2.53 (s, 3H). 13C NMR (75 MHz, DMSO-d6) $\delta$ 151.23, 147.50, 147.23, 133.38, 131.27, 129.47, 129.40, 128.55, 127.36, 126.41, 124.94, 123.31, 123.27, 123.08, 121.67, 118.09, 112.67, 51.42, 49.02, 35.6. UV-Vis (BPES Buffer, pH=7.2 with 1% SDS): $\lambda$max 427, $\varepsilon$=10,071 M−1 cm−1.

N1-methyl-N2-(9-nitrobenzo[c]acridin-7-yl)ethane-1,2-diamine (B2).

A suspension of B2.3 (298.2 mg, 0.814 mmol, 1 eq) and N-methylethylenediamine (0.150 mL, 1.720 mmol, 2.1 eq) was stirred at reflux in 10 mL of anhydrous dioxane for 24 h. After cooling to RT, the dioxane was removed by rotary evaporation and the residue was suspended in 2M NaOH. After 2 hours of stirring, the dark red solid was collected by vacuum filtration and washed with 2M NH4OH to afford a pure red solid (280 mg, 99%, ≥95% by LC-ESI-MS). 1H NMR (300 MHz, DMSO-d6) $\delta$ 9.47 (d, J=2.5 Hz, 1H), 9.30 (d, J=7.7 Hz, 1H), 8.36 (dd, J=9.4, 2.4 Hz, 1H), 8.19 (d, J=9.4 Hz, 1H), 8.10 (d, J=9.4 Hz, 1H), 8.01-7.92 (m, 1H), 7.85-7.66 (m, 3H), 3.96 (t, J=6.3 Hz, 2H), 2.93 (t, J=6.2 Hz, 2H), 2.33 (s, 3H). 13C NMR (75 MHz, DMSO-d6) $\delta$ 153.42, 149.57, 149.19, 141.41, 133.98, 130.76, 130.65, 129.36, 127.49, 126.74, 125.39, 123.87, 122.56, 122.35, 121.10, 114.94, 111.93, 50.96, 48.58, 35.62. UV-Vis (BPES Buffer, pH=7.2 with 1% SDS): $\lambda$max 441, $\varepsilon$=4,851 M−1 cm−1.

N1-methyl-N2-(10-nitrobenzo[c]acridin-7-yl)ethane-1,2-diamine (B3).

A suspension of B3.2 (251.0 mg, 0.814 mmol, 1 eq) and N-methylethylenediamine (0.141 mL, 1.617 mmol, 2 eq) was stirred at reflux in 4 mL of anhydrous dioxane for 24 h. After cooling to RT, the dioxane was removed by rotary evaporation and the residue was suspended in 2M NaOH. After 2 hours of stirring, the dark red solid was collected by vacuum filtration and washed with 2M NH4OH. This solid was dissolved in CHCl3 and washed with brine, followed by 4M NH4OH to remove excess N-methylethylenediamine. The organic layer was dried over Na2SO4 with activated carbon and filtered over celite. The chloroform in the filtrate was removed by rotary evaporation and the remaining solid dried in vacuo to afford the pure red solid (228.5 mg, 81%, ≥95% by LC-ESI-MS). 1H NMR (300 MHz, DMSO-d6) δ 9.39-9.23 (m, 1H), 8.82 (d, J=2.5 Hz, 1H), 8.65 (d, J=9.4 Hz, 1H), 8.31-8.02 (m, 2H), 8.04-7.87 (m, 1H), 7.88-7.68 (m, 3H), 3.87 (t, J=6.2 Hz, 2H), 2.86 (t, J=6.2 Hz, 2H), 2.30 (s, 3H). 13C NMR (75 MHz, DMSO-d6) δ 151.31, 148.87, 147.48, 146.22, 133.57, 130.75, 129.25, 127.54, 126.91, 126.21, 125.14, 125.06, 124.70, 121.23, 120.30, 115.16, 113.34, 51.22, 48.80, 35.64. UV-Vis BPES Buffer, pH=7.2 with 1% SDS): λmax 403, ε=6,922 M−1 cm−1.

[Pt(Cl)(NH3)2(N-(2-(acridin-9-ylamino)ethyl)-N-methyl-propionimidamide)] Cl P1-A1.

A solution of P1 (106.7 mg, 0.302 mmol, 1 eq.) and A1 (81.2 mg, 0.323 mmol, 1.1 eq) in 2 mL of anhydrous DMF was stored at −20° C. for 72 h. Activated carbon was added to the DMF solution, which was then filtered through a 0.2 μm membrane into vigorously stirring diethyl ether. The yellow precipitate was recovered by vacuum filtration, washed with diethyl ether, and dried in vacuo to afford a pure yellow solid (161.9 mg, 88%, ≥95% by LC-ESI-MS). 1H NMR (500 MHz, Methanol-d4) δ 8.25 (d, J=8.6 Hz, 2H), 7.92-7.55 (m, 5H), 7.35 (q, J=9.6, 7.5 Hz, 2H), 4.06 (t, J=6.4 Hz, 2H), 3.74 (t, J=6.3 Hz, 2H), 3.19-2.86 (m, 5H), 1.27 (t, J=7.5 Hz, 4H). 13C NMR (75 MHz, Methanol-d4) δ 171.62, 155.25, 132.36, 129.24, 126.62, 125.96, 123.66, 29.08, 11.53. HRMS (ESI—positive-ion mode) m/z for C19H28ClN6Pt [M]+, Calc: 570.1706; Found: 570.1073; Tolerance: 0.549 ppm.

[Pt(Cl)(NH3)2(N-(2-(benzo[c]acridin-7-ylamino)ethyl)-N-methylpropionimidamide)] Cl (P1-B1).

A solution of P1 (251.3 mg, 0.701 mmol, 1 eq.) and B1 (324.8 mg, 1.018 mmol, 1.4 eq) in 1.5 mL of anhydrous DMF was stirred at 4° C. for 4 days, after which it was slowly warmed to room temperature and allowed to stir for an additional 24 h. The DMF was removed by vacuum distillation in a 35° C. water bath and the resulting brown residue was dissolved in minimal anhydrous methanol and stirred with minimal activated carbon. This mixture was filtered through a 0.2 μm membrane into vigorously stirring diethyl ether and allowed to stir for 24 h. The yellow precipitate was recovered by vacuum filtration, washed with diethyl ether, and dried in vacuo to afford a yellow solid (385.2 mg, 83%, ≥90% by LC-ESI-MS). A small sample of this solid was further purified for biological testing by dissolving in anhydrous dichloromethane, filtering through celite, and recovering the solid from the filtrate by rotary evaporation (≥95% by LC-ESI-MS). 1H NMR (500 MHz, Methanol-d4) δ 9.24 (d, J=5.3 Hz, 1H), 8.35-8.22 (m, 1H), 8.23-8.12 (m, 1H), 8.00 (d, J=9.3 Hz, 1H), 7.92-7.79 (m, 1H), 7.79-7.43 (m, 5H), 3.87 (t, J=6.6 Hz, 2H), 3.66 (t, J=6.6 Hz, 2H), 2.92 (d, J=35.2 Hz, 7H), 1.22 (t, J=7.6 Hz, 3H). 13C NMR (126 MHz, Methanol-d4) δ 169.94, 151.27, 147.66, 134.07, 129.71, 128.69, 128.36, 127.48, 126.56, 124.82, 124.52, 124.07, 122.59, 120.54, 118.78, 113.90, 10.19. HRMS (ESI—positive-ion mode) m/z for C23H30ClN6Pt [M]+, Calc: 620.1863; Found: 620.1862; Tolerance: 0.134 ppm.

[Pt(Cl)(NH3)2(N-methyl-N-(2-((9-nitrobenzo[c]acridin-7-yl)amino)ethyl)propionimidamide)] Cl •1/3 DMF (P1-B2).

A solution of P1 (202.8 mg, 0.572 mmol, 1 eq.) and B2 (296.7 mg, 0.857 mmol, 1.5 eq) in 5 mL of anhydrous DMF was stirred at 4° C. for 4 days, after which it was slowly warmed to room temperature and allowed to stir for an additional 24 h. An orange precipitate formed which was recovered by vacuum filtration, and washed with anhydrous DMF and diethyl ether, and dried in vacuo to afford a dark orange solid (165.8 mg, 41%, ≥95% by LC-ESI-MS). 1H NMR (500 MHz, DMSO-d6) δ 9.49-9.38 (m, 1H), 9.31 (d, J=8.0 Hz, 1H), 8.40 (dd, J=9.4, 2.4 Hz, 1H), 8.20 (dd, J=32.7, 9.5 Hz, 2H), 8.07-7.67 (m, 4H), 6.13 (s, 1H), 4.29 (s, 3H), 3.98 (d, J=24.8 Hz, 5H), 3.81 (t, J=7.1 Hz, 2H), 3.02 (s, 5H), 1.24 (s, 3H). 13C NMR (126 MHz, DMSO-d6) δ 168.81, 153.25, 149.54, 149.42, 141.89, 134.07, 130.95, 130.85, 129.58, 127.69, 126.98, 125.46, 124.46, 122.55, 122.27, 121.18, 115.40, 112.64. HRMS (ESI—positive-ion mode) m/z for C23H29O2ClN7Pt [M]+, Calc: 665.1719; Found: 665.1701; Tolerance: 2.766 ppm.

Synthesis of Intermediates

[PtCl(NC3H5)(1,3-diaminopropane)]Cl (P3). [PtCl2(1,3diaminopropane)] (113.4 mg, 0.333 mmol) was suspended in pH=4 HCl (13 mL) with propionitrile (1.5 mL) and stirred at reflux for 1 h. The solvent was removed by rotary evaporation and the remaining residue was dried in vacuo with a 40° C. water bath for 1 h. The residue was dissolved in HPLC grade MeOH (3 mL) and filtered through a 0.2 μm filter into vigorously stirring anhydrous diethyl ether. The white precipitate stirred in diethyl ether for 2 h, and subsequently was collected by vacuum filtration, washed with anhydrous diethylether, and dried in vacuo to afford a pure white solid (110.3 mg, 84%). 1H NMR (300 MHz, Methanol-d4) δ 5.45 (d, J=58.1 Hz, 5H), 2.92 (q, J=7.5 Hz, 2H), 2.82-2.48 (m, 5H), 1.82 (p, J=5.4 Hz, 2H), 1.34 (t, J=7.5 Hz, 3H).

[PtCl(NC3H5)(N1,N1,N2,N2-tetramethylethane-1,2-diamine)] (P4). [PtCl2(N1,N1,N2,N2-tetramethylethane-1,2-diamine)] (115.8 mg, 0.303 mmol, 1 eq.) was suspended in pH=4 HCl (12 mL) with propionitrile (1.3 mL) and stirred at reflux for 2 h. The clear solution was cooled to room temperature and silver nitrate (50.0 mg, 0.294 mmol, 0.97 eq) was added. The solution was stirred in the dark for 20 min and filtered through a 0.2 μm membrane to remove silver chloride. The solvent was removed via rotary evaporation and dried for 1 h in vacuo with a 40° C. water bath. The residue was dissolved in HPLC grade MeOH (3 mL) and filtered through a 0.2 μm filter into vigorously stirring anhydrous diethyl ether. The white precipitate stirred in diethyl ether for 2 h, and subsequently was collected by vacuum filtration, washed with anhydrous diethylether, and dried in vacuo to afford a pure white solid (64.3 mg, 46%). 1H NMR (300 MHz, Methanol-d4) δ 3.11-2.77 (m, 17H), 1.36 (t, J=7.5 Hz, 3H).

4-phenoxyquinoline (Q1.1). Phenol (6.80, 72.3 mmol, 10.6 eq) and sodium hydroxide (403.9 mg, 10 mmol, 1.5 eq) were heated to 100° C. with stirring until all sodium hydroxide was dissolved. 4-chloroquinoline (1.1106 g, 6.8 mmol, 1 eq) was added neat to the sodium phenoxide solution. The reaction was stirred at 120° C. for 2 h. The solution was poured into vigorously stirring 2M sodium hydroxide. The resulting suspension was stirred for 30 min and the solid was collected by vacuum filtration. The solid was washed with 2M sodium hydroxide and minimal 4M NH4OH and dried in vacuo to afford the pure light yellow oil (1.4132 g, 94%). 1H NMR (300 MHz, Chloroform-d) δ 8.67 (d, J=5.1 Hz, 1H), 8.40-8.30 (m, 1H), 8.10 (d, J=8.6 Hz, 1H), 7.73 (ddd, J=8.3, 6.8, 1.5 Hz, 1H), 7.50 (dt, J=32.1, 7.8 Hz, 3H), 7.28 (d, J=7.4 Hz, 1H), 7.22-7.12 (m, 2H), 6.57 (d, J=5.2 Hz, 1H). 13C NMR was not obtained.

2-(naphthalen-1-ylamino)benzoic acid (B1.1). A round-bottom flask was charged with 1-napthylamine (20., 35.0825 g, 140.3 mmol, 1.2 eq), 2-chlorobenzoic acid (18.2710 g, 116.7 mmol, 1 eq), potassium acetate (41.1870 g, 419.6 mmol, 3.6 eq), copper(II) acetate monohydrate (2.6378 g, 13.2 mmol, 0.1 eq), and triethylamine (40 mL). The reagents were suspended in 200 mL of isopropanol and stirred at reflux for 60 h. After 60 h, the isopropanol was removed by roatary evaporation and the remaining residue was stirred in 2M HCl for 2 h. The resulting purple precipitate was collected by vacuum filtration and washed with copious amounts of distilled water. The crude solid was purified by flash chromatography on silica gel with dichloromethane as the eluent to produce a pure tan solid (9.7554 g, 32%). 1H NMR (300 MHz, DMSO-d6) δ 13.16 (s, 1H), 10.05 (s, 1H), 8.06-7.88 (m, 3H), 7.77 (dt, J=7.6, 3.8 Hz, 1H), 7.65-7.45 (m, 4H), 7.33 (ddd, J=8.7, 7.1, 1.7 Hz, 1H), 6.92 (dd, J=8.6, 1.0 Hz, 1H), 6.77 (ddd, J=8.1, 7.1, 1.1 Hz, 1H). 13C NMR (75 MHz, DMSO-d6) δ 170.29, 148.47, 136.04, 134.29, 134.16, 131.70, 128.52, 128.40, 126.32, 126.02, 124.49, 121.74, 119.67, 116.99, 113.71, 112.00.

7-chlorobenzo[c]acridine (B1.2). A suspension of B1.1 (773 mg, 2.936 mmol) was stirred at 80° C. with 5 mL phosphorus oxychloride for 2 h. Phosphorus oxychloride was removed by rotary evaporation and the remaining crude solid stirred in ice water. After 20 min, the solution was poured into ice-cold 50% NH4OH and stirred for 1 hour, gradually warming to room temperature. The solid was collected by vacuum filtration and washed with water to afford the pure tan solid (726.4 mg, 94%). 1H NMR (300 MHz, Chloroform-d) δ 9.56-9.35 (m, 1H), 8.49-8.29 (m, 2H), 8.19 (d, J=9.3 Hz, 1H), 7.92-7.59 (m, 6H). 13C NMR (75 MHz, Chloroform-d) δ 147.78, 147.52, 140.04, 133.54, 131.30, 130.11, 130.01, 129.42, 128.98, 127.94, 127.66, 126.95, 125.58, 124.77, 124.44, 122.65, 121.74.

7-phenoxybenzo[c]acridine (B1.3). Phenol (3.95 g, 41.9 mmol, 15 eq) and sodium hydroxide (148.2 mg, 3.705 mmol, 1.3 eq) were heated to 100° C. with stirring until all sodium hydroxide was dissolved. B1.2 (726.4 g, 2.754 mmol, 1 eq) was added neat to the sodium phenoxide solution. The reaction was stirred at 120° C. for 2 h. The solution was poured into vigorously stirring 2M sodium hydroxide. The resulting suspension was stirred for 30 min and the solid was collected by vacuum filtration. The solid was washed with 2M sodium hydroxide and minimal 4M NH4OH and dried in vacuo to afford the pure tan solid (867.5m g, 98%). 1H NMR (300 MHz, Chloroform-d) δ 9.58-9.42 (m, 1H), 8.40 (dt, J=8.8, 0.9 Hz, 1H), 8.10 (ddd, J=8.6, 1.5, 0.8 Hz, 1H), 7.90-7.67 (m, 5H), 7.61 (d, J=9.2 Hz, 1H), 7.50 (ddd, J=8.5, 6.7, 1.1 Hz, 1H), 7.32-7.16 (m, 2H), 7.08-6.97 (m, 1H), 6.92-6.81 (m, 2H). 13C NMR (75 MHz, Chloroform-d) δ 158.42, 153.18, 148.28, 148.10, 132.77, 130.51, 128.97, 128.93, 128.88, 128.22, 126.95, 126.81, 126.43, 124.98, 124.29, 121.43, 120.12, 118.65, 117.38, 114.44.

2-(naphthalen-1-ylamino)-5-nitrobenzoic acid (B2.1). A round-bottom flask was charged with 1-napthylamine (4.9989 g, 34.911 mmol, 1.2 eq), 2-chloro-5-nitrobenzoic acid (5.7062 g, 28.310 mmol, 1 eq), potassium acetate (10.30 g, 104.9 mmol, 3.7 eq), copper(II) acetate monohydrate (322.6 mg, 3.287 mmol, 0.12 eq), triethylamine (10 mL, 71.697 mmol, 2.5 eq), and isopropanol (200 mL). The mixture was stirred at reflux for 24 h, after which the reaction was filtered hot and washed with isopropanol. The resulting solid was stirred in 2M HCl, filtered, washed with DI H2O, and dried in vacuo to afford an orange solid (2.5944 g, 30%). 1H NMR (300 MHz, DMSO-d6) δ 10.64 (s, 1H), 8.76 (d, J=2.8 Hz, 1H), 8.13-7.99 (m, 2H), 8.01-7.83 (m, 2H), 7.67-7.50 (m, 5H), 6.68 (d, J=9.4 Hz, 1H). 13C NMR (75 MHz, DMSO-d6) δ 168.88, 153.72, 136.36, 134.24, 133.93, 129.25, 129.03, 128.54, 128.33, 127.07, 127.00, 126.66, 126.04, 123.21, 121.89, 113.40, 110.58.

9-nitro-7-chlorobenzo[c]acridine (B2.2). This intermediate was prepared analogously to intermediate B1.2. Starting from B2.1 (2.0984 g, 6.795 mmol) and phosphorus oxychloride (10 mL), B2.2 was obtained as an orange solid (1.4803 g, 73%). This product could not be characterized due to limited solubility.

9-nitro-7-phenoxybenzo[c]acridine (B2.3). This intermediate was prepared analogously to intermediate B1.3. Starting from B2.2 (702.3 mg, 2.25 mmol, 1 eq), phenol (3.3308 g, 35.393 mmol, 16 eq) and sodium hydroxide (128.5 mg, 3.213 mmol, 1.4 eq), B2.3 was obtained as an orange solid (722.6 mg, 87%). This product could not be characterized due to limited solubility.

2-(naphthalen-1-ylamino)-4-nitrobenzoic acid (B3.1). This intermediate was prepared analogously to intermediate B2.1. Starting from 1-napthylamine (5.08 g, 35.477 mmol, 1.25 eq), 2-chloro-4-nitrobenzoic acid (5.72 g, 28.379 mmol, 1 eq), potassium acetate (10.68 g, 108.813 mmol, 3.8 eq), copper(II) acetate monohydrate (0.28 g, 1.4024 mmol, 0.05 eq), triethylamine (10 mL) and isopropanol (125 mL), B3.1 was obtained as an orange solid and purified by flash chromatography on silica gel with dichloromethane as the eluent (2.5944 g, 30%). 1H NMR (300 MHz, DMSO-d6) δ 10.22 (s, 1H), 8.19 (d, J=8.6 Hz, 1H), 8.05 (dd, J=6.5, 2.8 Hz, 1H), 7.98 (dd, J=6.6, 2.3 Hz, 1H), 7.91 (dd, J=6.9, 2.2 Hz, 1H), 7.67-7.57 (m, 5H), 7.53-7.45 (m, 2H). 13C NMR not obtained.

10-nitro-7-chlorobenzo[c]acridine (B3.2). This intermediate was prepared analogously to intermediate B1.2. Starting from B3.1 (800 mg, 892.2 mg) and phosphorus oxychloride (10 mL), B3.2 was obtained as an orange solid (800.6 mg, 90%). This product could not be characterized due to limited solubility.

Determination of pKa Values for Platinum Complexes.

The pKa values of P1-A1, P1-B1 and P1-B2 were determined spectrophotometrically using a Hewlett Packard 8354 spectrophotometer equipped with a Peltier temperature control and a cell stirring module. Titrations were carried out at 25° C. in the pH range 2-11 with a micro combination electrode placed inside the cuvette. Solutions of P1-A1 (~100 μM), P1-B1 (~100 μM), and P1-B2 (~50 μM) in 0.1 M HCl/100 mM NaCl were titrated with aliquots of 0.4 M, 0.04M, and 0.004M KOH, and UV-Vis spectra were recorded after a 2 min equilibration time. The protonation state of the chromophores was deduced from spectral changes around isosbestic points. The pKa values were determined graphically from plots of pH vs. log[k(Aacr/AacrH+)], where k=εacrH+/εacr using suitable absorbance maxima. The pKa values of P1-A1 and P1-B1 were determined at the y-intercept of the plot. P1-B2 titration to the free base resulted in a competing equilibrium of dimer formation, so the pKa was determined by finding the inflection point of the titration plot. Reported pKa values are means of three measurements+/−the standard deviation.

Cell Culture.

The human non-small cell lung cancer cell lines, NCI-H460 (large cell), NCI-H520 (squamous cell), NCI-H522, NCI-H1435 and A549 (adenocarcinomas) were obtained from the American Type Culture Collection (Rockville, Md., USA). NCI-H460, NCI-H520 and NCI-H522 cells were cultured in RPMI-1640 media (HyClone) supplemented with 10% fetal bovine serum (FBS), 10% penstrep (P&S), 10% L-glutamine, and 1.5 g/L $NaHCO_3$. A549 cells were cultured in HAM's F12K media (Gibco) with the same additives as above. NCI-H1435 cells were cultured in serum-free 1:1 DMEM/F12 media (Gibco) containing 2.436 g/L $NaHCO_3$, 0.02 mg/mL insulin, 0.01 mg/mL transferrin, 25 nM sodium selenite, 50 nM hydrocortisone, 1 ng/mL epidermal growth factor, 0.01 mM ethanolamine, 0.01 mM phosphorylethanolamine, 100 pM triiodothyronine, 0.5% (w/v) bovine serum albumin (BSA), 10 mM HEPES, 0.5 mM sodium pyruvate, and an extra 2 mM L-glutamine (final concentration 4.5 mM). Cells were incubated at a constant temperature at 37° C. in a humidified atmosphere containing 5% $CO_2$ and were subcultured every 2 to 3 days in order to maintain cells in logarithmic growth, except for NCI-H1435 which was subcultured every 7 days.

Cytotoxicity Assay.

The cytotoxicity studies were carried out according to a standard protocol using the Celltiter 96 aqueous nonradioactive cell proliferation assay kit (Promega, Madison, Wis.). Stock solutions (10 mM) of all drugs were made in DMF, except for P1-B2 which was made in DMSO, and serially diluted with media prior to incubation with cancer cells. $IC_{50}$ values were calculated from nonlinear curve fits using a sigmoidal dose-response equation in GraphPad Prism (GraphPad Software, La Jolla, Calif.).

In an embodiment, the present invention relates to compounds of Formulas I and II, to compositions (e.g., pharmaceutical compositions) containing those compounds and to methods of using those compounds.

In an embodiment, the pharmaceutical composition may contain pharmaceutically acceptable salts, solvates, and prodrugs thereof, and may contain diluents, excipients, carriers, or other substances necessary to increase the bioavailability or extend the lifetime of the compounds of the present invention.

Subjects that may be treated by the compounds and compositions of the present invention include, but are not limited to, horses, cows, sheep, pigs, mice, dogs, cats, primates such as chimpanzees, gorillas, rhesus monkeys, and, humans. In an embodiment, a subject is a human in need of cancer treatment.

The pharmaceutical compositions containing a compound of the invention may be in a form suitable for injection either by itself or alternatively, using liposomes, micelles, and/or nanospheres.

The pharmaceutical composition suitable for injection can be made as disclosed in Lammers, T. et al., J. Controlled Release, 161, 175-187 (2012), or in Barenholz, Y., J. Controlled Release, 160, 117-134, (2012), both of which are incorporated by reference in their entireties. Alternatively, compositions intended for injection may be prepared according to any known method, and such compositions may contain one or more agents selected from the group consisting of solvents, co-solvents, solubilizing agents, wetting agents, suspending agents, emulsifying agents, thickening agents, chelating agents, antioxidants, reducing agents, antimicrobial preservatives, buffers, pH adjusting agents, bulking agents, protectants, tonicity adjustors, and special additives. Moreover, other non-toxic pharmaceutically-acceptable excipients which are suitable for the manufacture of injectables may be used.

Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycethanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate.

The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, sterile water for injection (SWFI), Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

Thus, in another embodiment, the present invention provides a pharmaceutical formulation solution comprising a compound of Formula I or of Formula II or a salt thereof.

A solution of the invention may be provided in a sealed container, especially one made of glass, either in a unit dosage form or in a multiple dosage form.

Any pharmaceutically acceptable salt of a compound of Formula I or II may be used for preparing a solution of the invention. Examples of suitable salts may be, for instance, the salts with mineral inorganic acids such as hydrochloric, hydrobromic, sulfuric, phosphoric, nitric and the like, and the salts with certain organic acids such as acetic, succinic, tartaric, ascorbic, citric, glutamic, benzoic, methanesulfonic, ethanesulfonic and the like. In an embodiment, the compound of Formula I is a hydrochloric acid salt including a mono, di, or trihydrochloride.

Any solvent which is pharmaceutically acceptable and which is able to dissolve the compounds of Formula I or II or a pharmaceutically acceptable salt thereof may be used. The solution of the invention may also contain one or more additional components such as a co- solubilizing agent (which may be the same as a solvent), a tonicity adjustment agent, a stabilizing agent, a preservative, or mixtures thereof. Examples of solvents, co-solubilizing agents, tonicity adjustment agents, stabilizing agents and preservatives which may suitable for a solution formulation are described below.

Suitable solvents and co-solubilizing agents may include, but are not limited to, water; sterile water for injection (SWFI); physiological saline; alcohols, e.g. ethanol, benzyl alcohol and the like; glycols and polyalcohols, e.g. propyleneglycol, glycerin and the like; esters of polyalcohols, e.g. diacetine, triacetine and the like; polyglycols and polyethers, e.g. polyethyleneglycol 400, propyleneglycol methylethers and the like; dioxolanes, e.g. isopropylidenglycerin and the like; dimethylisosorbide; pyrrolidone derivatives, e.g. 2-pyrrolidone, N-methyl-2-pyrrolidone, polyvinylpyrrolidone (co-solubilizing agent only) and the like; polyoxyethylenated fatty alcohols; esters of polyoxyethylenated fatty acids; polysorbates, e.g., Tween™, polyoxyethylene derivatives of polypropyleneglycols, e.g., Pluronics™.

Suitable tonicity adjustment agents may include, but are not limited to, pharmaceutically acceptable inorganic chlorides, e.g. sodium chloride; dextrose; lactose; mannitol; sorbitol and the like.

Preservatives suitable for physiological administration may be, for instance, esters of parahydroxybenzoic acid (e.g., methyl, ethyl, propyl and butyl esters, or mixtures of them), chlorocresol and the like.

Suitable stabilizing agents include, but are not limited to, monosaccharides (e.g., galactose, fructose, and fucose), disaccharides (e.g., lactose), polysaccharides (e.g., dextran), cyclic oligosaccharides (e.g., alpha-, beta-, gamma-cyclodextrin), aliphatic polyols (e.g., mannitol, sorbitol, and thioglycerol), cyclic polyols (e.g. inositol) and organic solvents (e.g., ethyl alcohol and glycerol).

The above mentioned solvents and co-solubilizing agents, tonicity adjustment agents, stabilizing agents and preservatives can be used alone or as a mixture of two or more of them in a solution formulation.

In an embodiment, a pharmaceutical solution formulation may comprise a compound of Formula I or II or a pharmaceutically acceptable salt thereof, and an agent selected from the group consisting of sodium chloride solution (i.e., physiological saline), dextrose, mannitol, or sorbitol, wherein the agent is in an amount of less than or equal to 5%. The pH of such a formulation may also be adjusted to improve the storage stability using a pharmaceutically acceptable acid or base.

In the solutions of the invention the concentration of the compound of Formula I or II or a pharmaceutically acceptable salt thereof may be less than 100 mg/mL, or less than 50 mg/mL, or less than 10 mg/mL, or less than 10 mg/mL and greater than 0.01 mg/mL, or between 0.5 mg/mL and 5 mg/mL, or between 1 mg/mL and 3 mg/mL. In an embodiment, the concentration that is used is the ideal concentration to be sufficiently cytotoxic to the cancer cells yet limit the toxicity on other cells.

Suitable packaging for the pharmaceutical solution formulations may be all approved containers intended for parenteral use, such as plastic and glass containers, ready-to-use syringes and the like. In an embodiment, the container is a sealed glass container, e.g. a vial or an ampoule. A hermetically sealed glass vial is particularly preferred.

According to an embodiment of the present invention, there is provided, in a sealed glass container, a sterile, injectable solution comprising a compound of Formula I or a pharmaceutically acceptable salt thereof in a physiologically acceptable solvent, and which has a pH of from 2.5 to 3.5. For solution formulations, various compounds of the present invention may be more soluble or stable for longer periods in solutions at a pH lower than 6. Further, acid salts of the compounds of the present invention may be more soluble in aqueous solutions than their free base counter parts, but when the acid salts are added to aqueous solutions the pH of the solution may be too low to be suitable for administration. Thus, solution formulations having a pH above pH 4.5 may be combined prior to administration with a diluent solution of pH greater than 7 such that the pH of the combination formulation administered is pH 4.5 or higher. In one embodiment, the diluent solution comprises a pharmaceutically acceptable base such as sodium hydroxide. In another embodiment, the diluent solution is at pH of between 10 and 12. In another embodiment, the pH of the combined formulation administered is greater than 5.0. In another embodiment, the pH of the combined formulation administered is between pH 5.0 and 7.0.

The invention also provides a process for producing a sterile solution with a pH of from 2.5 to 3.5 which process comprises dissolving a compound of Formula I or a pharmaceutically acceptable salt thereof in a pharmaceutically acceptable solvent. Where a pharmaceutically acceptable acid salt of a compound of Formula I is used the pH of the solution may be adjusted using a pharmaceutically acceptable base or basic solution adding a physiologically acceptable acid or buffer to adjust the pH within a desired range. The method may further comprise passing the resulting solution through a sterilizing filter.

One or more additional components such as co-solubilizing agents, tonicity adjustment agents, stabilizing agents and preservatives, for instance of the kind previously specified, may be added to the solution prior to passing the solution through the sterilizing filter.

In a further variation, the present invention contemplates combination therapies in which the compounds of the present invention can be used in conjunction with other cisplatin compounds. The efficacy of this combination therapy is likely to be enhanced because of the different mechanisms and modes of action that first generation cisplatin compounds exhibit relative to the compounds of the present invention. It is also contemplated and therefore within the scope of the invention that other anti-neoplastic agents/compounds can be used in conjunction with the compounds of the present invention. The anti-neoplastic agents/compounds that can be used with the compounds of the present invention include cytotoxic compounds as well as non-cytotoxic compounds.

Examples include anti-tumor agents such as HERCEPTIN™ (trastuzumab), RITUXAN™ (rituximab), ZEVALIN™ (ibritumomab tiuxetan), LYMPHOCIDE™ (epratuzumab), GLEEVAC™ and BEXXAR™ (iodine 131 tositumomab).

Other anti-neoplastic agents/compounds that can be used in conjunction with the compounds of the present invention include anti-angiogenic compounds such as ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto).

Other anti-angiogenic compounds/agents that can be used in conjunction with the compounds of the present invention include Campath, IL-8, B-FGF, Tek antagonists, anti-TWEAK agents (e.g., specifically binding antibodies or antigen binding regions, or soluble TWEAK receptor antagonists, ADAM distintegrin domain to antagonize the binding of integrin to its ligands, specifically binding anti-eph receptor and/or anti-ephrin antibodies or antigen binding regions, and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Other anti-angiogenic/anti-tumor agents that can be used in conjunction with the compounds of the present invention include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA); ilomastat, (Arriva, USA,); emaxanib, (Pfizer, USA,); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland); the ARGENT technology of Ariad, USA; YIGSR-Stealth, (Johnson & Johnson, USA); fibrinogen-E fragment, (BioActa, UK); the angiogenesis inhibitors of Trigen, UK; TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (WVAX, USA); Benefin, (Lane Labs, USA); Tz-93, (Tsumura, Japan); TAN-1120, (Takeda, Japan); FR-111142, (Fujisawa, Japan); platelet factor 4, (RepliGen, USA); vascular endothelial growth factor antagonist, (Borean, Denmark); bevacizumab (pINN), (Genentech, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Children's Hospital, USA); ATN 161, (Attenuon, USA); ANGIOSTATIN, (Boston Children's Hospital, USA); 2-methoxyestradiol, (Boston Children's Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Children's Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrugs, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pIN), (Genaera, USA); RPI 4610, (Sima, USA); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

It is contemplated and therefore within the scope of the invention that the compounds of the present invention can be modified to target specific receptors or cancer cells or can be modified so that they can survive various in vivo environments. As examples, the compounds of the present invention can be modified so that they are combined with dendrimers or other cyclic sugars to form carboxylate dendrimers or other sugars. They may be combined with steroids such as estrogen to form carboxylate steroids like carboxylate estrogen. If the compounds of the present invention contain carboxylate functionalities, the carboxylate functionalities on these compounds may be modified so that they contain folic acid. Those of skill in the art will recognize that there are other modifications that can be made to the compounds of the present invention so that they can target specific receptors, cells or provide stability to the compounds. It is contemplated that the compounds of the present invention can have modifications made that are covalent modifications, ionic modifications, modified so that they chelate to other compounds, or other undergo some other type of interaction that allows the compounds of the present invention to suit their use (such as hydrophobic or Van der Waals type interactions).

In a further variation, the compounds of the present invention can be used against solid tumors, cell lines, and cell line tissue that demonstrate upregulated nucleotide excision repair and other upregulated resistance mechanisms.

Thus, the present invention relates to compounds of Formula I, and pharmaceutically acceptable salts and solvates thereof:

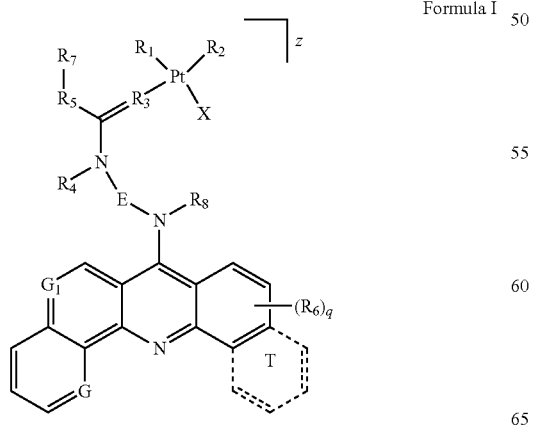

Formula I wherein X is halo, OC(O)R$_9$, nitrate or sulfate;

R$_1$ and R$_2$ are amino groups or together with the platinum atom to which they are attached, R$_1$ and R$_2$ form the ring —NH$_2$—(CH$_2$)$_v$—NH$_2$— wherein v is 1, 2, 3, or 4 or R$_1$ and R$_2$ together can be any of the following groups a-h;

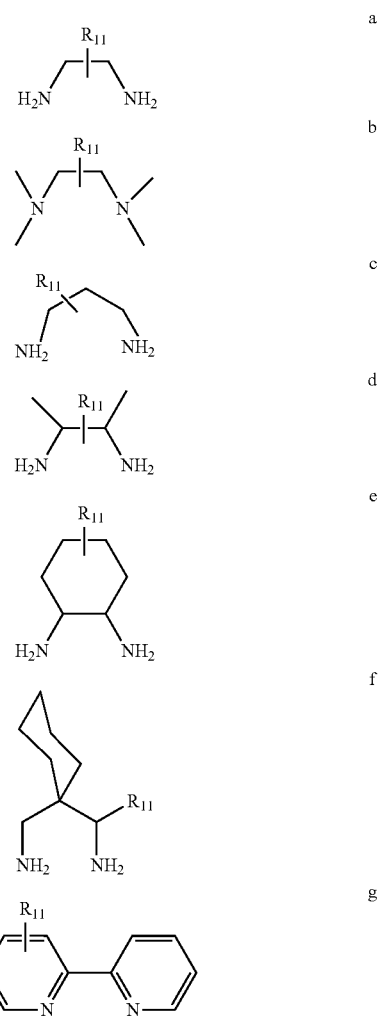

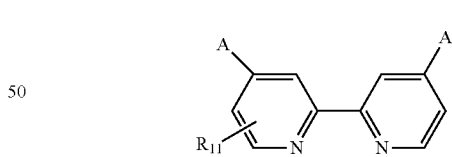

wherein A is H, —CH$_3$, —OCH$_3$, CF$_3$ or NO$_2$;
R$_3$ is —N(R$_{26}$)—; wherein R$_{26}$ is hydrogen or C$_1$-C$_6$alkyl;
R$_4$ is hydrogen, C$_{1-6}$ alkyl, or CH$_2$—R$_{12}$;
R$_6$ is independently an amino, a nitro, —NHC(O)(R$_{10}$), —NHC(O)O(R$_{10}$), —C(O)NHR$_{10}$, —OC(O)NHR$_{10}$, or halo;
R$_{10}$ is hydrogen, C$_{1-6}$ alkyl, phenyl, naphthyl, C$_{3-6}$ cycloalkyl, norbornyl, or adamantyl;
q is 0, 1, or 2;
R$_5$ is a direct bond, —NH— or C$_1$-C$_6$alkylene;

or $R_5$ and X together with the atoms to which they are attached form a 6- or 7-membered ring, wherein said 6- or 7-membered ring contains a linking group —C(O)O— or —OC(O)—;

$R_7$ is hydrogen, methyl, —CH($R_{17}$)($R_{18}$), —C(O)O—$R_{18}$, or —OC(O)—$R_{18}$; wherein $R_{17}$ is hydrogen or $C_{1-6}$ alkyl;

$R_{18}$ is hydrogen, $C_{1-6}$ alkyl, —CH($R_{19}$)($R_{20}$), phenyl, naphthyl, $C_{3-6}$ cycloalkyl, norbornyl, adamantyl, a natural or unnatural amino acid or a peptide;

$R_{19}$ is hydrogen or $C_{1-6}$ alkyl;

$R_{20}$ is hydrogen, $C_{1-6}$ alkyl;

$R_8$ is —H or -$C_{1-6}$alkyl;

$R_9$ is hydrogen, $C_{1-6}$ alkyl, phenyl, naphthyl, $C_{3-6}$ cycloalkyl, norbornyl, adamantyl, a natural or unnatural amino acid or a peptide;

$R_{11}$ and $R_{12}$ are independently hydrogen, hydroxyl, $C_{1-6}$ alkyl, —OCH$_3$, —CF$_3$, NO$_2$, —N$_3$, —COOH, —CONH$_2$, —CH=CH$_2$, —C≡CH, —(CH$_2$)$_{1-6}$—OH, —(CH$_2$)$_{1-6}$—N$_3$, —(CH$_2$)$_{1-6}$—COOH, —(CH$_2$)$_{1-6}$—CH=CH$_2$, —(CH$_2$)$_{1-6}$—C≡CH, —(CH$_2$)$_{0-1}$(—OCH$_2$CH$_2$)$_{1-6}$—OH, —(CH$_2$)$_{0-1}$(—OCH$_2$CH$_2$)$_{1-6}$—N$_3$, or —(CH$_2$)$_{0-1}$(—OCH$_2$CH$_2$)$_{1-6}$—COOH or either or both of $R_{11}$ and $R_{12}$ contain a reactive group on to which a linker and/or one or more of compound W can be added;

E is $C_1$-$C_6$alkylene;

G and $G_1$ are independently N or CR$_{16}$;

$R_{16}$ is hydrogen or methyl;

compound W is one or more amino acids, one or more sugars, polymeric ethers, $C_{1-6}$alkylene-phenyl—NH—C(O)—$R_{15}$, folic acid, $α_vβ_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof; and Z is independently one or more halo or nitro, or one or more counterions sufficient to balance the charge of the compound;

wherein $R_{15}$ is a peptide; and the benzene ring which is T is optionally present.

In an embodiment, the present invention relates to compounds, pharmaceutically acceptable salts or solvates, wherein $R_{11}$ and $R_{12}$ combined with the linker and compound W are —NH—$R_{13}$,

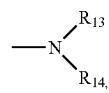

—O—$R_{13}$, —CH=CH—$R_{13}$, —C≡C—$R_{13}$,

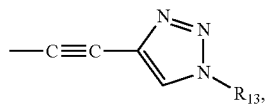

—N$_3$, —COOH, —COOR$_{14}$, —C(O)NH—$R_{13}$, —NHC(O)—$R_{13}$, —OC(O)NH—$R_{13}$, —OC(O)O—$R_{13}$, —(CH$_2$)$_{1-6}$—NH—$R_{13}$,

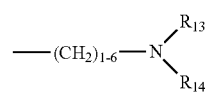

—(CH$_2$)$_{1-6}$—O—$R_{13}$, —(CH$_2$)$_{1-6}$—N$_3$, —(CH$_2$)$_{1-6}$—COOH, —(CH$_2$)$_{1-6}$—COOR$_{14}$ or —(CH$_2$)$_{1-6}$—CH=CH—$R_{13}$;

wherein $R_{13}$ and $R_{14}$ are independently selected from the group consisting of one or more amino acids, one or more sugars, polymeric ethers, PAMAM (Poly(amido amine)) Dendrimers such as carboxylate-modified PAMAM Dendrimers, PLGA (poly(lactic-co-glycolic acid)), -triazol-$R_{15}$, $C_{1-6}$alkylene-phenylene—NH—C(O)—$R_{15}$, folic acid, fatty acid, and polyunsaturated fatty acid (PUFA), $α_vβ_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof; wherein $R_{15}$ is a peptide.

In a variation, the present invention relates to compounds, pharmaceutically acceptable salts, or solvates wherein G and $G_1$ are C. Alternatively, G is NH and $G_1$ is C. Alternatively, G is C and $G_1$ is NH.

In an embodiment, T is not present.

In an embodiment, the present invention relates to compounds, pharmaceutically acceptable salts, or solvates, wherein the compound is a compound of Formula II:

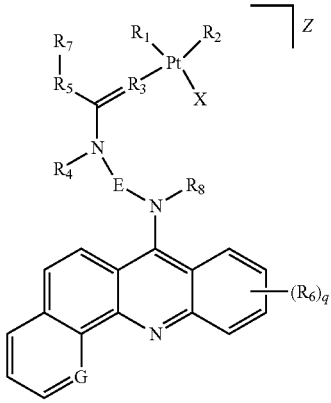

Formula II wherein X is halo, OC(O)R$_9$, nitrate or sulfate;

$R_1$ and $R_2$ are amino groups or together with the platinum atom to which they are attached, $R_1$ and $R_2$ form the ring —NH$_2$—(CH$_2$)$_v$—NH$_2$— wherein v is 1, 2, 3, or 4 or $R_1$ and $R_2$ together can be any of the following groups a-h;

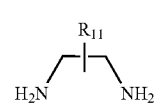
a

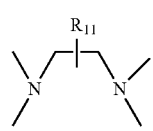
b

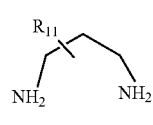
c

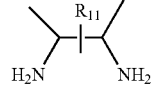
d

-continued

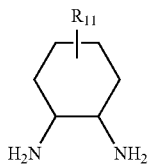

e

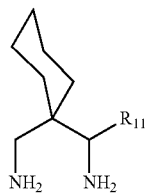

f

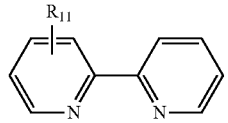

g

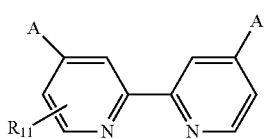

h wherein A is H, —CH$_3$, —OCH$_3$, CF$_3$ or NO$_2$;
R$_3$ is —N(R$_{26}$)—; wherein R$_{26}$ is hydrogen or C$_1$-C$_6$alkyl;
R$_4$ is hydrogen, C$_{1-6}$ alkyl, or CH$_2$—R$_{12}$;
R$_6$ is independently an amino, a nitro, —NHC(O)(R$_{10}$), —NHC(O)O(R$_{10}$), —C(O)NHR$_{10}$, —OC(O)NHR$_{10}$, or halo;
R$_{10}$ is hydrogen, C$_{1-6}$ alkyl, phenyl, naphthyl, C$_{3-6}$ cycloalkyl, norbornyl, or adamantyl;
q is 0, 1, or 2;
R$_5$ is a direct bond, —NH— or C$_1$-C$_6$alkylene;
or R$_5$ and X together with the atoms to which they are attached form a 6- or 7-membered ring, wherein said 6- or 7-membered ring contains a linking group —C(O)O— or —OC(O)—;
R$_7$ is hydrogen, methyl, —CH(R$_{17}$)(R$_{18}$), —C(O)O—R$_{18}$, or —OC(O)—R$_{18}$; wherein
R$_{17}$ is hydrogen or C$_{1-6}$ alkyl;
R$_{18}$ is hydrogen, C$_{1-6}$ alkyl, —CH(R$_{19}$)(R$_{20}$), phenyl, naphthyl, C$_{3-6}$ cycloalkyl, norbornyl, adamantyl, a natural or unnatural amino acid or a peptide;
R$_{19}$ is hydrogen or C$_{1-6}$ alkyl;
R$_{20}$ is hydrogen, C$_{1-6}$ alkyl;
R$_8$ is —H or -C$_{1-6}$alkyl;
R$_9$ is hydrogen, C$_{1-6}$ alkyl, phenyl, naphthyl, C$_{3-6}$ cycloalkyl, norbornyl, adamantyl, a natural or unnatural amino acid or a peptide;
R$_{11}$ and R$_{12}$ are hydrogen, C$_{1-6}$ alkyl, phenyl, naphthyl, C$_{3-6}$ cycloalkyl, norbornyl, adamantyl, a natural or unnatural amino acid or a peptide;
E is C$_1$-C$_6$alkylene;
G is N or CR$_{16}$;
R$_{16}$ is hydrogen or methyl;
compound W is one or more amino acids, one or more sugars, polymeric ethers, C$_{1-6}$alkylene-phenyl—NH—C(O)—R$_{15}$, folic acid, $\alpha_v\beta_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof; and
Z is independently one or more halo or nitro, or one or more counterions sufficient to balance the charge of the compound.

In an embodiment, when the compounds, pharmaceutically acceptable salts, or solvates are the compounds, salts or solvates of Formula II, R$_{11}$ and R$_{12}$ combined with the linker and compound W may be
—NH—R$_{13}$,

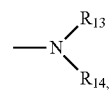

—O—R$_{13}$, —CH=CH—R$_{13}$, —C≡C—R$_{13}$,

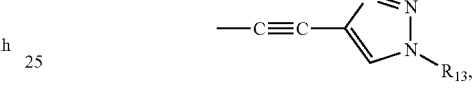

—N$_3$, —COOH, —COOR$_{14}$, —C(O)NH—R$_{13}$, —NHC(O)—R$_{13}$, —OC(O)NH—R$_{13}$, —OC(O)O—R$_{13}$, —(CH$_2$)$_{1-6}$—NH—R$_{13}$,

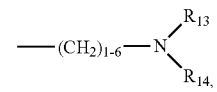

—(CH$_2$)$_{1-6}$—O—R$_{13}$, —(CH$_2$)$_{1-6}$—N$_3$, —(CH$_2$)$_{1-6}$—COOH, —(CH$_2$)$_{1-6}$—COOR$_{14}$ or —(CH$_2$)$_{1-6}$—CH=CH—R$_{13}$;

In an embodiment, the present invention relates to pharmaceutical compositions comprising a compound, pharmaceutically acceptable salt or solvate of Formula I:

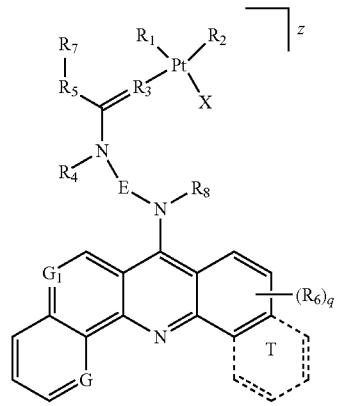

Formula I wherein X is halo, OC(O)$_9$, nitrate or sulfate;
R$_1$ and R$_2$ are amino groups or together with the platinum atom to which they are attached, R$_1$ and R$_2$ form the ring —NH$_2$—(CH$_2$)$_v$—NH$_2$— wherein v is 1, 2, 3, or 4 or R$_1$ and R$_2$ together can be any of the following groups a-h;

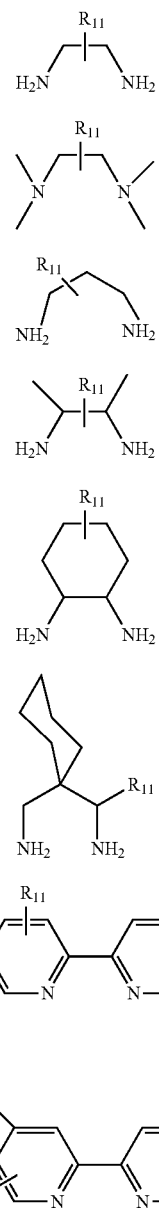

wherein A is H, —CH₃, —OCH₃, CF₃ or NO₂;
$R_3$ is —N($R_{26}$)—; wherein $R_{26}$ is hydrogen or $C_1$-$C_6$alkyl;
$R_4$ is hydrogen, $C_{1-6}$ alkyl, or CH₂—$R_{12}$;
$R_6$ is independently an amino, a nitro, —NHC(O)($R_{10}$), —NHC(O)O($R_{10}$), —C(O)NH$R_{10}$, —OC(O)NH$R_{10}$, or halo;
$R_{10}$ is hydrogen, $C_{1-6}$ alkyl, phenyl, naphthyl, $C_{3-6}$ cycloalkyl, norbornyl, or adamantyl;
q is 0, 1, or 2;
$R_5$ is a direct bond, —NH— or $C_1$-$C_6$alkylene;
or $R_5$ and X together with the atoms to which they are attached form a 6- or 7-membered ring, wherein said 6- or 7-membered ring contains a linking group —C(O)O— or —OC(O)—;
$R_7$ is hydrogen, methyl, —CH($R_{17}$)($R_{18}$), —C(O)O—$R_{18}$, or —OC(O)—$R_{18}$; wherein $R_{17}$ is hydrogen or $C_{1-6}$ alkyl;
$R_{18}$ is hydrogen, $C_{1-6}$ alkyl, —CH($R_{19}$)($R_{20}$), phenyl, naphthyl, $C_{3-6}$ cycloalkyl, norbornyl, adamantyl, a natural or unnatural amino acid or a peptide;
$R_{19}$ is hydrogen or $C_{1-6}$ alkyl;
$R_{20}$ is hydrogen, $C_{1-6}$ alkyl;
$R_8$ is —H or -$C_{1-6}$alkyl;
$R_9$ is hydrogen, $C_{1-6}$ alkyl, phenyl, naphthyl, $C_{3-6}$ cycloalkyl, norbornyl, adamantyl, a natural or unnatural amino acid or a peptide;
$R_{11}$ and $R_{12}$ are independently hydrogen, hydroxyl, $C_{1-6}$ alkyl, —OCH₃, —CF₃, NO₂, —N₃, —COOH, —CONH₂, —CH=CH₂, —C≡CH, —(CH₂)$_{1-6}$—OH, —(CH₂)$_{1-6}$—N₃, —(CH₂)$_{1-6}$—COOH, —(CH₂)$_{1-6}$—CH=CH₂, —(CH₂)$_{1-6}$—C≡CH, —(CH₂)$_{0-1}$(—OCH₂CH₂)$_{1-6}$—OH, —(CH₂)$_{0-1}$(—OCH₂CH₂)$_{1-6}$—N₃, or —(CH₂)$_{0-1}$(—OCH₂CH₂)$_{1-6}$—COOH or either or both of $R_{11}$ and $R_{12}$ contain a reactive group on to which a linker and/or one or more of compound W can be added;
E is $C_1$-$C_6$alkylene;
G and $G_1$ are independently N or CR$_{16}$;
$R_{16}$ is hydrogen or methyl;
compound W is one or more amino acids, one or more sugars, polymeric ethers, $C_{1-6}$alkylene-phenyl—NH—C(O)—$R_{15}$, folic acid, $\alpha_v\beta_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof; and
Z is independently one or more halo or nitro, or one or more counterions sufficient to balance the charge of the compound; and wherein
wherein $R_{15}$ is a peptide;
the benzene ring which is T is optionally present, and one or more diluents, excipients, carriers, or substance that increases bioavailability or extends a lifetime of the compound.

In the various pharmaceutical compositions, G may be NH or C and $G_1$ may be C. Alternatively, G may be NH and $G_1$ may be NH or C.

In a variation, T is not present.

In an embodiment, the present invention relates to a pharmaceutical composition, wherein the compound is a compound of Formula II:

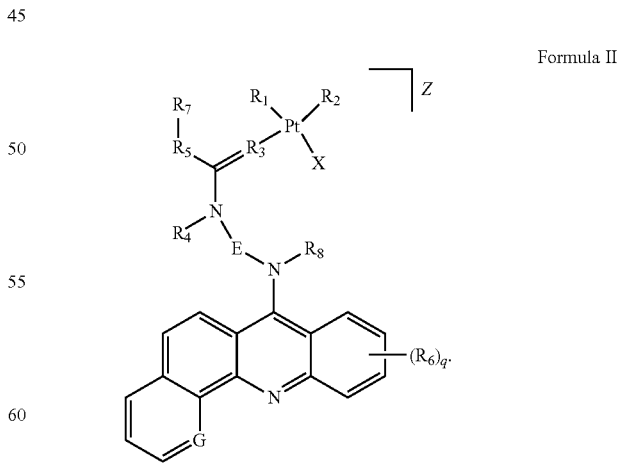

Formula II

In an embodiment, the present invention relates to a method of treating cancer in an individual in need thereof comprising administering to said individual a compound of Formula I:

Formula I

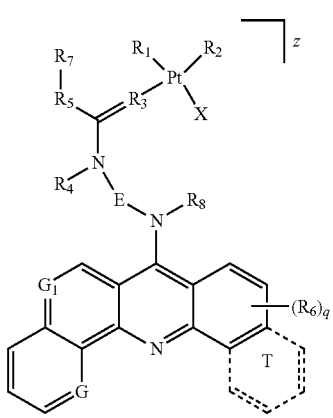

wherein X is halo, OC(O)R$_9$, nitrate or sulfate;

R$_1$ and R$_2$ are amino groups or together with the platinum atom to which they are attached, R$_1$ and R$_2$ form the ring —NH$_2$—(CH$_2$)$_v$—NH$_2$— wherein v is 1, 2, 3, or 4 or R$_1$ and R$_2$ together can be any of the following groups a-h;

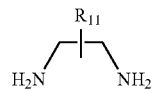
a

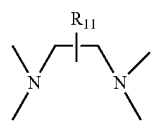
b

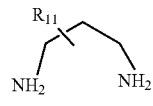
c

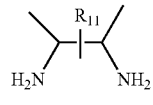
d

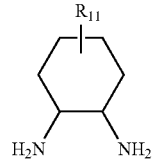
e

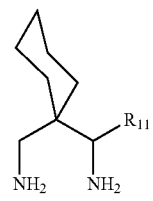
f

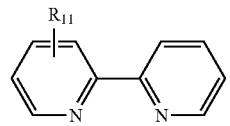
g

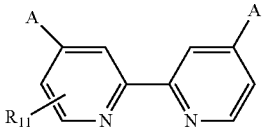
h wherein A is H, —CH$_3$, —OCH$_3$, CF$_3$ or NO$_2$;

R$_3$ is —N(R$_{26}$)—; wherein R$_{26}$ is hydrogen or C$_1$-C$_6$alkyl;

R$_4$ is hydrogen, C$_{1-6}$ alkyl, or CH$_2$—R$_{12}$;

R$_6$ is independently an amino, a nitro, —NHC(O)(R$_{10}$), —NHC(O)O(R$_{10}$), —C(O)NHR$_{10}$, —OC(O)NHR$_{10}$, or halo;

R$_{10}$ is hydrogen, C$_{1-6}$ alkyl, phenyl, naphthyl, C$_{3-6}$ cycloalkyl, norbornyl, or adamantyl;

q is 0, 1, or 2;

R$_5$ is a direct bond, —NH— or C$_1$-C$_6$alkylene;

or R$_5$ and X together with the atoms to which they are attached form a 6- or 7-membered ring, wherein said 6- or 7-membered ring contains a linking group —C(O)O— or —OC(O)—;

R$_7$ is hydrogen, methyl, —CH(R$_{17}$)(R$_{18}$), —C(O)O—R$_{18}$, or —OC(O)—R$_{18}$; wherein R$_{17}$ is hydrogen or C$_{1-6}$ alkyl;

R$_{18}$ is hydrogen, C$_{1-6}$ alkyl, —CH(R$_{19}$)(R$_{20}$), phenyl, naphthyl, C$_{3-6}$ cycloalkyl, norbornyl, adamantyl, a natural or unnatural amino acid or a peptide;

R$_{19}$ is hydrogen or C$_{1-6}$ alkyl;

R$_{20}$ is hydrogen, C$_{1-6}$ alkyl;

R$_8$ is —H or -C$_{1-6}$alkyl;

R$_9$ is hydrogen, C$_{1-6}$ alkyl, phenyl, naphthyl, C$_{3-6}$ cycloalkyl, norbornyl, adamantyl, a natural or unnatural amino acid or a peptide;

R$_{11}$ and R$_{12}$ are independently hydrogen, hydroxyl, C$_{1-6}$ alkyl, —OCH$_3$, —CF$_3$, NO$_2$, —N$_3$, —COOH, —CONH$_2$, —CH=CH$_2$, —C≡CH, —(CH$_2$)$_{1-6}$—OH, —(CH$_2$)$_{1-6}$—N$_3$, —(CH$_2$)$_{1-6}$—COOH, —(CH$_2$)$_{1-6}$—CH=CH$_2$, —(CH$_2$)$_{1-6}$—C≡CH, —(CH$_2$)$_{0-1}$(—OCH$_2$CH$_2$)$_{1-6}$—OH, —(CH$_2$)$_{0-1}$(—OCH$_2$CH$_2$)$_{1-6}$—N$_3$, or —(CH$_2$)$_{0-1}$(—OCH$_2$CH$_2$)$_{1-6}$—COOH or either or both of R$_{11}$ and R$_{12}$ contain a reactive group on to which a linker and/or one or more of compound W can be added;

E is C$_1$-C$_6$alkylene;

G and G$_1$ are independently N or CR$_{16}$;

R$_{16}$ is hydrogen or methyl;

compound W is one or more amino acids, one or more sugars, polymeric ethers, C$_{1-6}$alkylene-phenyl—NH—C(O)—R$_{15}$, folic acid, α$_v$β$_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof; and Z is independently one or more halo or nitro, or one or more counterions sufficient to balance the charge of the compound; and wherein wherein R$_{15}$ is a peptide; and the benzene ring which is T is optionally present.

In an embodiment, the method may use a compound of Formula II:

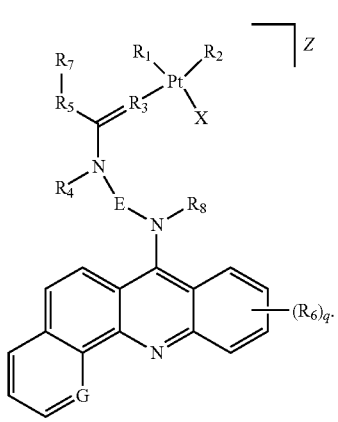

Formula II

In one embodiment, the cancer to be treated is small-cell lung cancer.

It is contemplated and therefore within the scope of the present invention that any feature that is disclosed in the present invention can be combined with any other feature in the present invention. For example, if a variable is described with reference to formula I, it should be recognized that it is contemplated and therefore within the scope of the present invention that the defined variable can also be used with Formula II. It is also contemplated that minor modifications can be made to the present invention.

The following references are incorporated by reference in their entireties:

(1) Kelland, L. *Nat Rev Cancer* 2007, 7, 573.
(2) Wang, X.; Guo, Z. *Chem Soc Rev* 2013, 42, 202.
(3) Martins, E. T.; Baruah, H.; Kramarczyk, J.; Saluta, G.; Day, C. S.; Kucera, G. L.; Bierbach, U. *J Med Chem* 2001, 44, 4492.
(4) Ma, Z.; Choudhury, J. R.; Wright, M. W.; Day, C. S.; Saluta, G.; Kucera, G. L.; Bierbach, U. *J Med Chem* 2008, 51, 7574.
(5) Ma, Z.; Rao, L.; Bierbach, U. *J Med Chem* 2009, 52, 3424.
(6) Baruah, H.; Wright, M. W.; Bierbach, U. *Biochemistry* 2005, 44, 6059.
(7) Kostrhunova, H.; Malina, J.; Pickard, A. J.; Stepankova, J.; Vojtiskova, M.; Kasparkova, J.; Muchova, T.; Rohlfing, M. L.; Bierbach, U.; Brabec, V. *Mol Pharm* 2011, 8, 1941.
(8) van Zutphen, S.; Reedijk, J. *Coordination Chemistry Reviews* 2005, 249, 2845.
(9) Hurley, L. H. *Nat Rev Cancer* 2002, 2, 188.
(10) Hurley, L. H. *Nature Reviews Cancer* 2002, 2, 188.
(11) Hurley, L. H.; Wheelhouse, R. T.; Sun, D.; Kerwin, S. M.; Salazar, M.; Fedoroff, O. Y.; Han, F. X.; Han, H.; Izbicka, E.; Von Hoff, D. D. *Pharmacol. Ther.* 2000, 85, 141.
(12) Sun, D.; Hurley, L. H. *Journal of Medicinal Chemistry* 2009, 52, 2863.
(13) Brooks, T. A.; Hurley, L. H. *Nature Reviews Cancer* 2009, 9, 849.
(14) Balasubramanian, S.; Hurley, L. H.; Neidle, S. *Nature Reviews Drug Discovery* 2011, 10, 261.
(15) Cogoi, S.; Xodo, L. E. *Nucl. Acids Res.* 2006, 34, 2536.
(16) Arora, A.; Kumar, N.; Agarwal, T.; Maiti, S. *FEBS Journal* 2010, 277, 1345.
(17) Bearss, D. J.; Hurley, L. H.; Von Hoff, D. D. *Oncogene* 2000, 19, 6632.
(18) Cairns, D.; Anderson, R. J.; Perry, P. J.; Jenkins, T. C. *Current Pharmaceutical Design* 2002, 8, 2491.
(19) Pickard, A. J.; Bierbach, U. *ChemMedChem* 2013, 8, 1441.
(20) Monchaud, D.; Teulade-Fichou, M. P. *Organic & Biomolecular Chemistry* 2008, 6, 627.
(21) Reha, D.; Kabelac, M.; Ryjacek, F.; Sponer, J.; Sponer, J. E.; Elstner, M.; Suhai, S.; Hobza, P. *J Am Chem Soc* 2002, 124, 3366.
(22) Berman, H. M.; Young, P. R. *Annu Rev Biophys Bioeng* 1981, 10, 87.
(23) Pindur, U.; Haber, M.; Sattler, K. *J Chem Educ* 1993, 70, 263.
(24) Muller, W.; Crothers, D. M.; Waring, M. J. *Eur J Biochem* 1973, 39, 223.
(25) Koeppel, F.; Riou, J. F.; Laoui, A.; Mailliet, P.; Arimondo, P. B.; Labit, D.; Petitgenet, O.; Helene, C.; Mergny, J. L.o *Nucleic Acids Res* 2001, 29, 1087.
(26) Kern, J. T.; Kerwin, S. M. *Bioorganic & Medicinal Chemistry Letters* 2002, 12, 3395.
(27) Ding, S.; Qiao, X.; Kucera, G. L.; Bierbach, U. *J Med Chem* 2012, 55, 10198.
(28) Weaver, D. A.; Crawford, E. L.; Warner, K. A.; Elkhairi, F.; Khuder, S. A.; Willey, J. C. *Mol Cancer* 2005, 4, 18.
(29) Ndolo, R. A.; Luan, Y.; Duan, S.; Forrest, M. L.; Krise, J. P. *PLoS One* 2012, 7, e49366.
(30) Dennington, R.; Keith, T.; Millam, J.; Semichem Inc.: Shawnee Mission KS, 2009.
(31) Becke, A. D. *The Journal of Chemical Physics* 1993, 98, 5648.
(32) Lee, C.; Yang, W.; Parr, R. G. *Physical Review B* 1988, 37, 785.
(33) Miertus, S.; Scrocco, E.; Tomasi, J. *Chemical Physics* 1981, 55, 117.

We claim:

1. A method of treating non-small cell lung cancer in an individual in need thereof comprising administering to said individual a compound of Formula I:

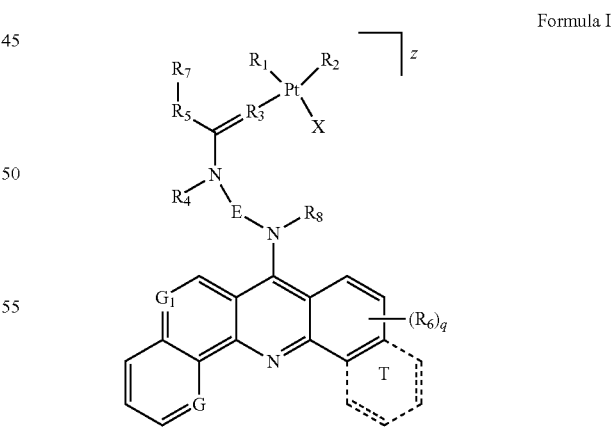

Formula I wherein X is halo, $OC(O)R_9$, nitrate or sulfate;

$R_1$ and $R_2$ are amino groups or together with the platinum atom to which they are attached, $R_1$ and $R_2$ form the ring $-NH_2-(CH_2)_v-NH_2-$ wherein v is 1, 2, 3, or 4 or $R_1$ and $R_2$ together can be any of the following groups a-h;

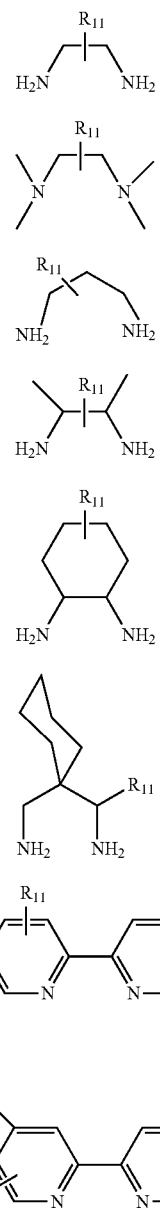

a b c d e f g h wherein A is H, —CH$_3$, —OCH$_3$, CF$_3$ or NO$_2$;

R$_3$ is —N(R$_{26}$)—; wherein R$_{26}$ is hydrogen or C$_1$-C$_6$alkyl;

R$_4$ is hydrogen, C$_{1-6}$ alkyl, or CH$_2$—R$_{12}$;

R$_6$ is independently an amino, a nitro, —NHC(O)(R$_{10}$), —NHC(O)O(R$_{10}$), —C(O)NHR$_{10}$, —OC(O)NHR$_{10}$, or halo;

R$_{10}$ is hydrogen, C$_{1-6}$ alkyl, phenyl, naphthyl, C$_{3-6}$ cycloalkyl, norbornyl, or adamantyl;

q is 0, 1, or 2;

R$_5$ is a direct bond, —NH— or C$_1$-C$_6$alkylene;

or R$_5$ and X together with the atoms to which they are attached form a 6- or 7-membered ring, wherein said 6- or 7-membered ring contains a linking group —C(O)O— or —OC(O)—;

R$_7$ is hydrogen, methyl, —CH(R$_{17}$)(R$_{18}$), —C(O)O—R$_{18}$, or —OC(O)—R$_{18}$; wherein R$_{17}$ is hydrogen or C$_{1-6}$ alkyl;

R$_{18}$ is hydrogen, C$_{1-6}$ alkyl, —CH(R$_{19}$)(R$_{20}$), phenyl, naphthyl, C$_{3-6}$ cycloalkyl, norbornyl, adamantyl, a natural or unnatural amino acid or a peptide;

R$_{19}$ is hydrogen or C$_{1-6}$ alkyl;

R$_{20}$ is hydrogen, C$_{1-6}$ alkyl;

R$_8$ is —H or -C$_{1-6}$alkyl;

R$_9$ is hydrogen, C$_{1-6}$ alkyl, phenyl, naphthyl, C$_{3-6}$ cycloalkyl, norbornyl, adamantyl, a natural or unnatural amino acid or a peptide;

R$_{11}$ and R$_{12}$ are independently hydrogen, hydroxyl, C$_{1-6}$ alkyl, —OCH$_3$, —CF$_3$, NO$_2$, —N$_3$, —COOH, —CONH$_2$, —CH=CH$_2$, —C≡CH, —(CH$_2$)$_{1-6}$—OH, —(CH$_2$)$_{1-6}$—N$_3$, —(CH$_2$)$_{1-6}$—COOH, —(CH$_2$)$_{1-6}$—CH=CH$_2$, —(CH$_2$)$_{1-6}$—C≡CH, —(CH$_2$)$_{0-1}$(—OCH$_2$CH$_2$)$_{1-6}$—OH, —(CH$_2$)$_{0-1}$(—OCH$_2$CH$_2$)$_{1-6}$—N$_3$, or —(CH$_2$)$_{0-1}$(—OCH$_2$CH$_2$)$_{1-6}$—COOH or either or both of R$_{11}$ and R$_{12}$ contain a reactive group on to which a linker and/or one or more of compound W can be added;

E is C$_1$-C$_6$alkylene;

G and G$_1$ are independently N or CR$_{16}$;

R$_{16}$ is hydrogen or methyl;

compound W is one or more amino acids, one or more sugars, polymeric ethers, C$_{1-6}$alkylene-phenyl—NH—C(O)—R$_{15}$, folic acid, α$_v$β$_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof; and Z is independently one or more halo or nitro, or one or more counterions sufficient to balance the charge of the compound; and wherein wherein R$_{15}$ is a peptide; and the benzene ring which is T is optionally present.

2. The method of claim 1, wherein the compound is a compound of Formula II:

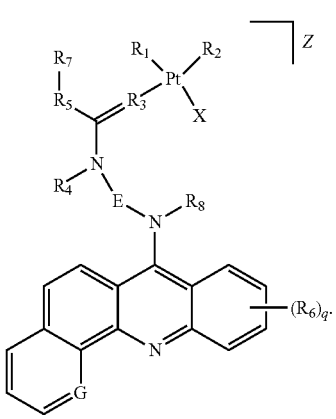

Formula II

3. A method of preparing a compound of Formula I comprising a platinum-containing component and a chromophore-containing component, Formula I

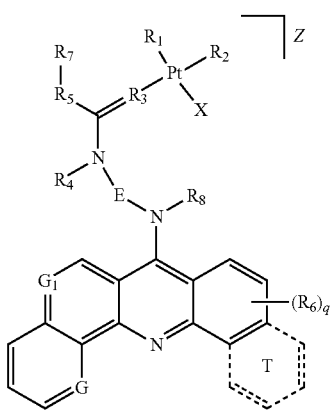

wherein:

(a) in the platinum-containing component,

X is halo, OC(O)R$_9$, nitrate or sulfate;

R$_1$ and R$_2$ are amino groups or together with the platinum atom to which they are attached, R$_1$ and R$_2$ form the ring —NH$_2$—(CH$_2$)$_v$—NH$_2$— wherein v is 1, 2, 3, or 4 or R$_1$ and R$_2$ together can be any of the following groups a-h;

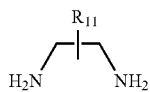

a

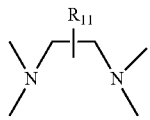

b

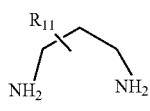

c

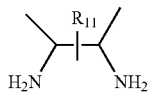

d

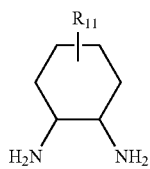

e

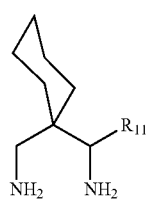

f

-continued

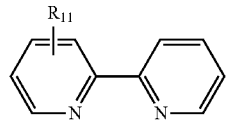

g

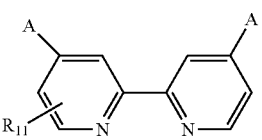

h wherein A is H, —CH$_3$, —OCH$_3$, CF$_3$ or NO$_2$;

R$_3$ is —N(R$_{26}$)—; wherein R$_{26}$ is hydrogen or C$_1$-C$_6$alkyl;

R$_5$ is a direct bond, —NH— or C$_1$-C$_6$alkylene;

or R$_5$ and X together with the atoms to which they are attached form a 6- or 7-membered ring, wherein said 6- or 7-membered ring contains a linking group —C(O)O— or —OC(O)—;

R$_7$ is hydrogen, methyl, —CH(R$_{17}$)(R$_{18}$), —C(O)O—R$_{18}$, or —OC(O)—R$_{18}$; wherein R$_{17}$ is hydrogen or C$_{1-6}$ alkyl;

R$_{18}$ is hydrogen, C$_{1-6}$ alkyl, —CH(R$_{19}$)(R$_{20}$), phenyl, naphthyl, C$_{3-6}$ cycloalkyl, norbornyl, adamantyl, a natural or unnatural amino acid or a peptide;

R$_{19}$ is hydrogen or C$_{1-6}$ alkyl;

R$_{20}$ is hydrogen, C$_{1-6}$ alkyl;

R$_9$ is hydrogen, C$_{1-6}$ alkyl, phenyl, naphthyl, C$_{3-6}$ cycloalkyl, norbornyl, adamantyl, a natural or unnatural amino acid or a peptide;

R$_{11}$ is hydrogen, hydroxyl, C$_{1-6}$ alkyl, —OCH$_3$, —CF$_3$, NO$_2$, —N$_3$, —COOH, —CONH$_2$, —CH=CH$_2$, —C≡CH, —(CH$_2$)$_{1-6}$—OH, —(CH$_2$)$_{1-6}$—N$_3$, —(CH$_2$)$_{1-6}$—COOH, —(CH$_2$)$_{1-6}$—CH=CH$_2$, —(CH$_2$)$_{1-6}$—C≡CH, —(CH$_2$)$_{0-1}$(—OCH$_2$CH$_2$)—OH, —(CH$_2$)$_{0-1}$(—OCH$_2$CH$_2$)$_{1-6}$—N$_3$, or —(CH$_2$)$_{0-1}$(—OCH$_2$CH$_2$)$_{1-6}$—COOH or R$_{11}$ contain a reactive group on to which a linker and/or one or more of compound W can be added;

compound W is one or more amino acids, one or more sugars, polymeric ethers, C$_{1-6}$alkylene-phenyl—NH—C(O)—R$_{15}$, folic acid, α$_v$β$_3$ integrin RGD binding peptide, tamoxifen, endoxifen, EGFR (epidermal growth factor receptor) antibody conjugates, kinase inhibitors, diazoles, triazoles, oxazoles, erlotinib, and mixtures thereof; wherein R$_{15}$ is a peptide; and Z is independently one or more halo or nitro, or one or more counterions sufficient to balance the charge of the compound;

and (b) in the chromophore-containing component,

R$_4$ is hydrogen, C$_{1-6}$ alkyl, or CH$_2$—R$_{12}$;

R$_{12}$ is hydrogen, hydroxyl, C$_{1-6}$ alkyl, —OCH$_3$, —CF$_3$, NO$_2$, —N$_3$, —COOH, —CONH$_2$, —CH=CH$_2$, —C≡CH, —(CH$_2$)$_{1-6}$—OH, —(CH$_2$)$_{1-6}$—N$_3$, —(CH$_2$)$_{1-6}$—COOH, —(CH$_2$)$_{1-6}$—CH=CH$_2$, —(CH$_2$)$_{1-6}$—C≡CH, —(CH$_2$)$_{0-1}$(—OCH$_2$CH$_2$)—OH, —(CH$_2$)$_{0-1}$(—OCH$_2$CH$_2$)$_{1-6}$—N$_3$, or —(CH$_2$)$_{0-1}$(—OCH$_2$CH$_2$)$_{1-6}$—COOH, or either or both of R$_{11}$ and $R_{12}$ contain a reactive group on to which a linker and/or one or more of compound W can be added;

$R_6$ is independently an amino, a nitro, —NHC(O)($R_{10}$), —NHC(O)O($R_{10}$), —C(O)NH$R_{10}$, —OC(O)NH$R_{10}$, or halo;

$R_{10}$ is hydrogen, $C_{1-6}$ alkyl, phenyl, naphthyl, $C_{3-6}$ cycloalkyl, norbornyl, or adamantyl;

q is 0, 1, or 2;

$R_8$ is —H or -$C_{1-6}$alkyl;

E is $C_1$-$C_6$alkylene;

G and $G_1$ are independently N or $CR_{16}$;

$R_{16}$ is hydrogen or methyl; and the benzene ring which is T is optionally present;

comprising reacting a chromophore with a platinum nitrile complex, wherein the chromophore is a precursor of the chromophore-containing component and the platinum nitrile complex is a precursor of the platinum-containing component.

4. The method of claim 3, wherein the platinum nitrile complex is selected from the group consisting of

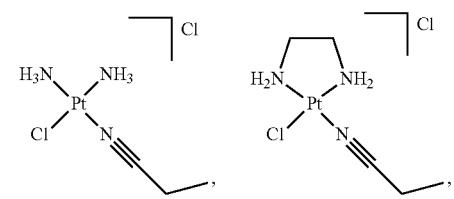

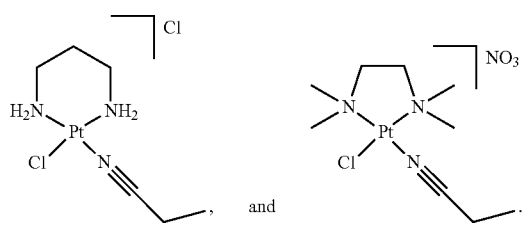

5. The method of claim 3, wherein the chromophore is selected from the group consisting of

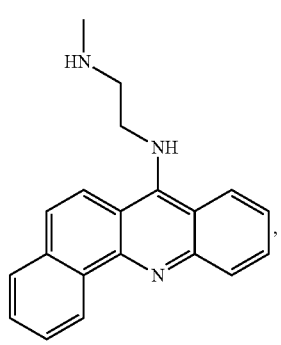

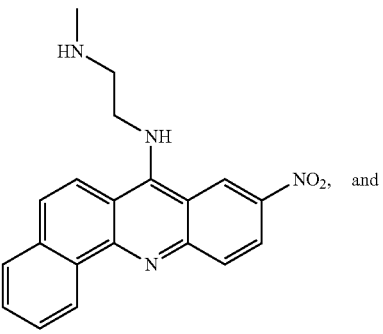

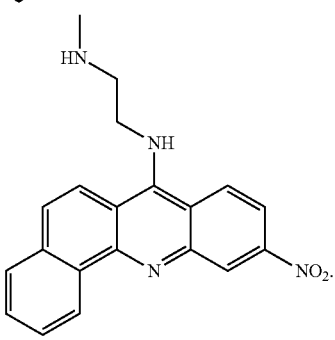

6. The method of claim 5, wherein the chromophore is derived from

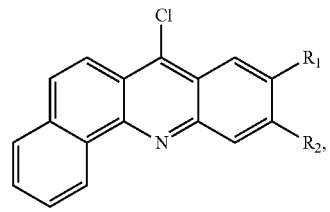

wherein $R_1$ and $R_2$ are each H;

$R_1$ is $NO_2$ and $R_2$ is H; or $R_1$ and $R_2$ are each $NO_2$.

7. The method of claim 5, wherein the chromophore is derived from

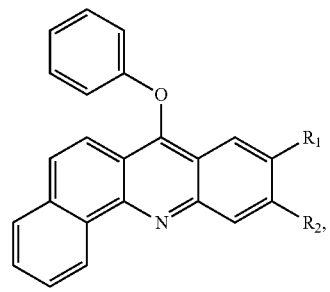

wherein $R_1$ and $R_2$ are each H; or $R_1$ is $NO_2$ and $R_2$ is H.

8. The method of claim 3, wherein the chromophore is
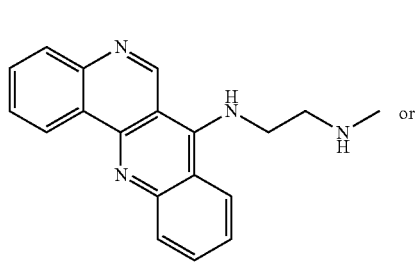
B4.6
or
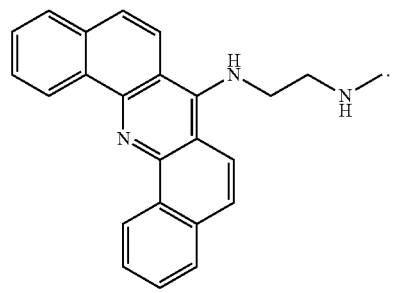
B5.4
9. The method of claim 8, wherein the chromophore is
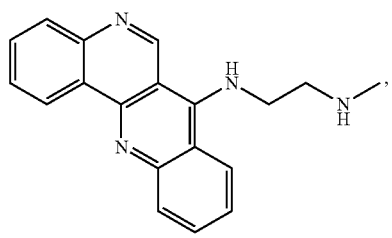
B4.6
which is derived from
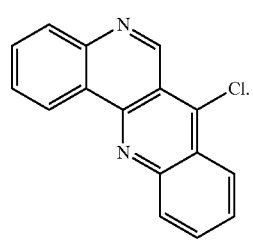
B4.4
10. The method of claim 8, wherein the chromophore is
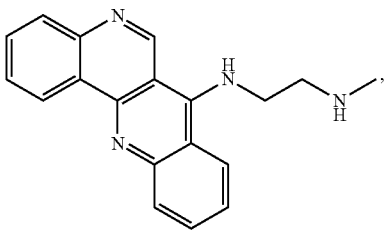
B4.6
which is derived from the reaction between
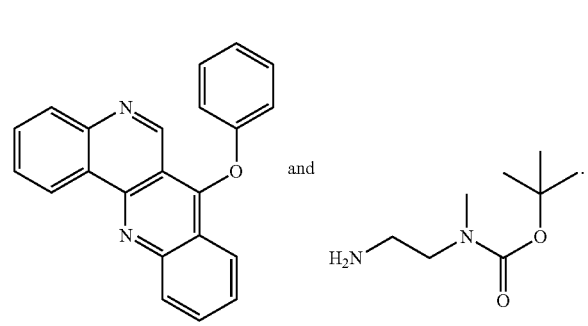 [SMILES: c1ccc(Oc2c3ccccc3nc3c2cnc2ccccc23)cc1 ; CN(CCN)C(=O)OC(C)(C)C]
and
11. The method of claim 8, wherein the chromophore is
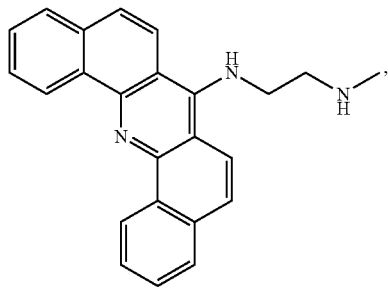 [SMILES: CNCCNc1c2ccc3ccccc3c2nc2c1ccc1ccccc12]
which is derived from
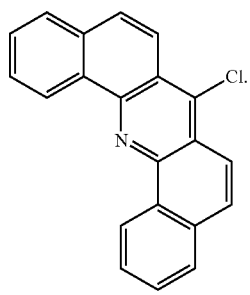 [SMILES: Clc1c2ccc3ccccc3c2nc2c1ccc1ccccc12]

12. The method of claim 8, wherein the chromophore is
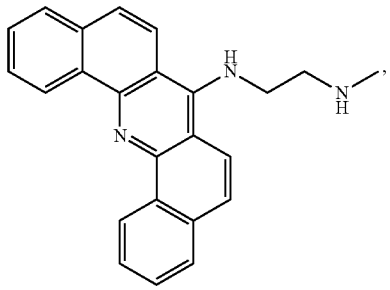 [SMILES: CNCCNc1c2ccc3ccccc3c2nc2c1ccc1ccccc12]
which is derived from the reaction between
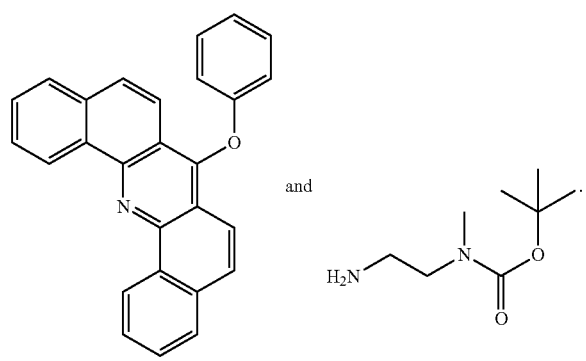 [SMILES: c1ccc(Oc2c3ccc4ccccc4c3nc3c2ccc2ccccc23)cc1 ; CN(CCN)C(=O)OC(C)(C)C]
13. The method of claim 3, wherein the chromophore is derived from an intermediate selected from the group consisting of
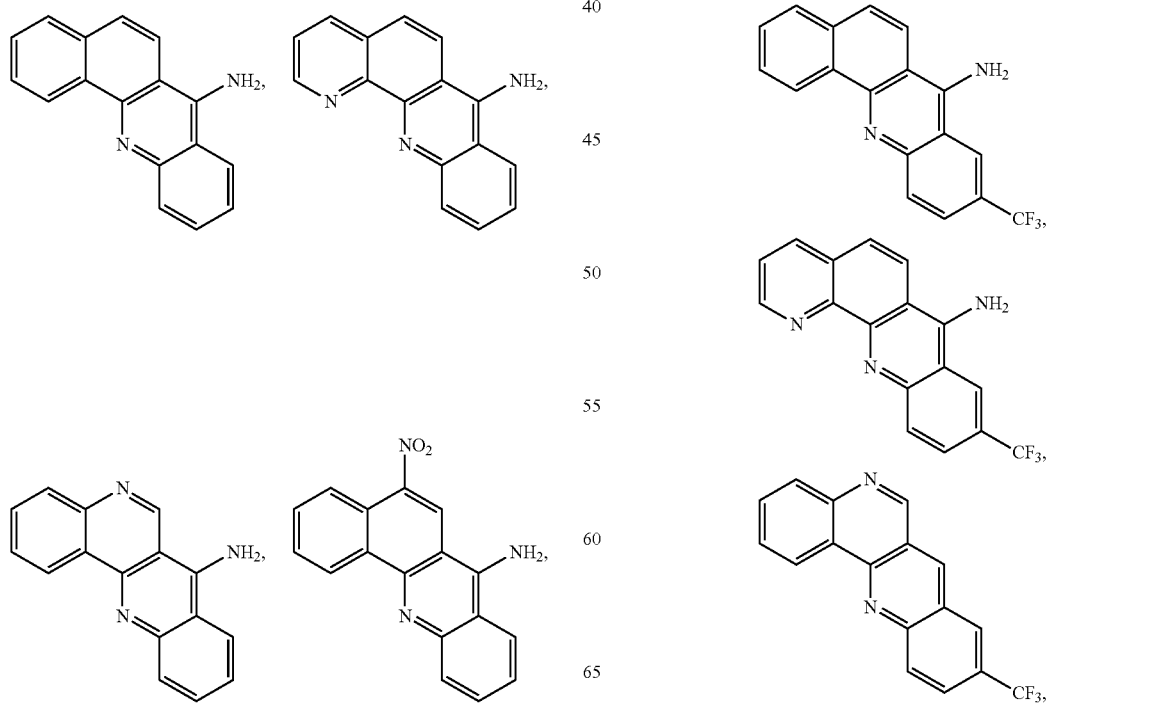

-continued
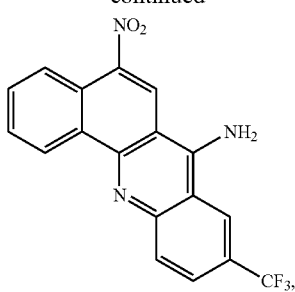
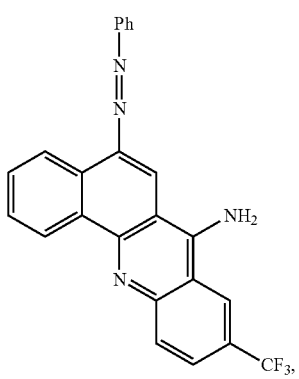
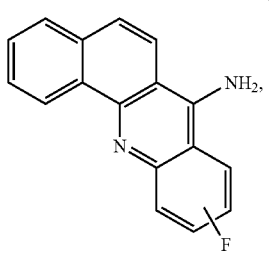
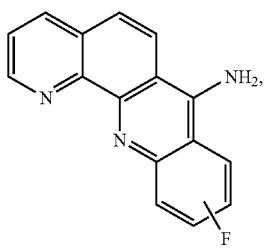
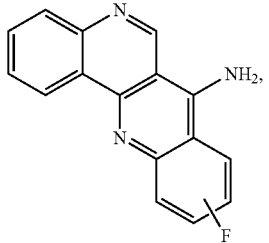
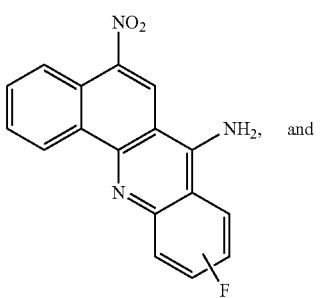, and
-continued
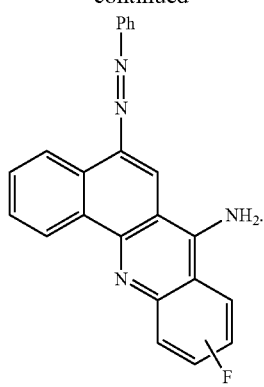
14. A compound prepared by the reaction between a platinum nitrile complex and a chromophore, wherein the platinum nitrile complex is selected from the group consisting of
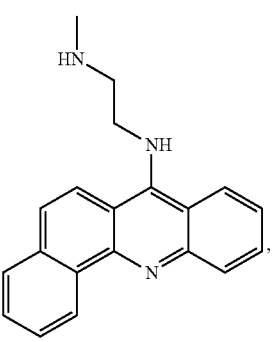
and
the chromophore is selected from the group consisting of -continued
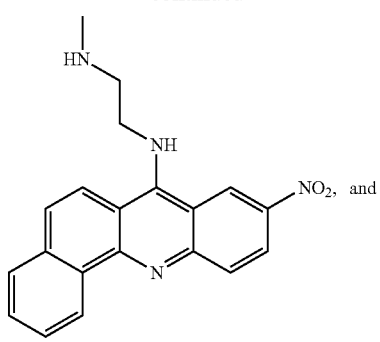
NO₂, and
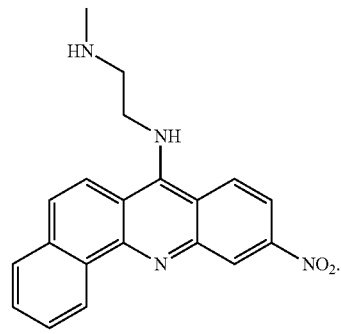
NO₂.
15. The compound of claim 14, wherein the chromophore is
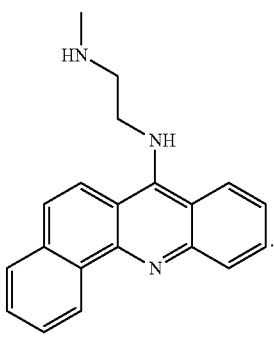 [SMILES: CNCCNc1c2ccccc2nc2c1ccc1ccccc12]
16. The compound of claim 14, wherein the platinum nitrile complex is
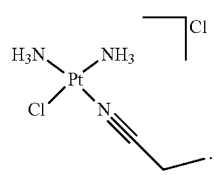
17. A compound selected from the group consisting of
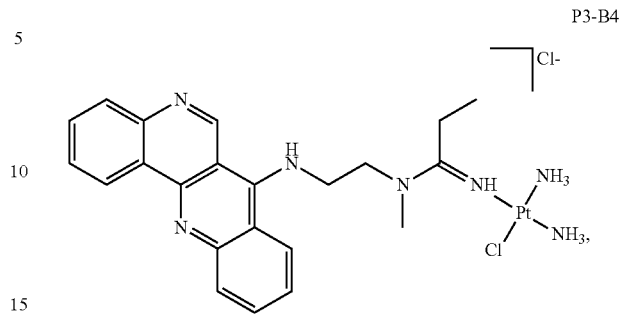
P3-B4
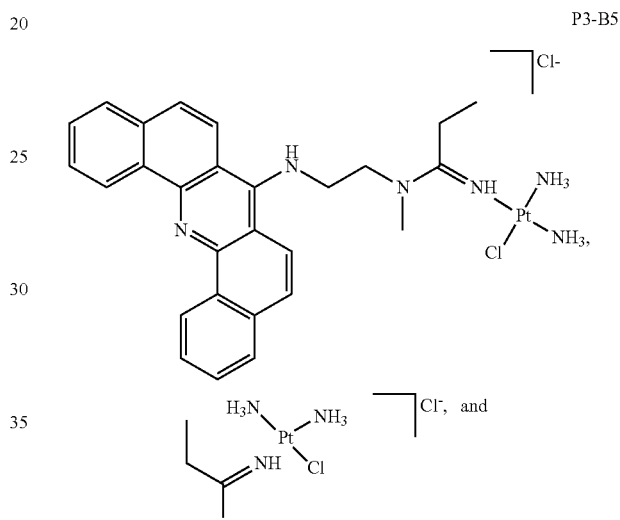
P3-B5
Cl⁻, and
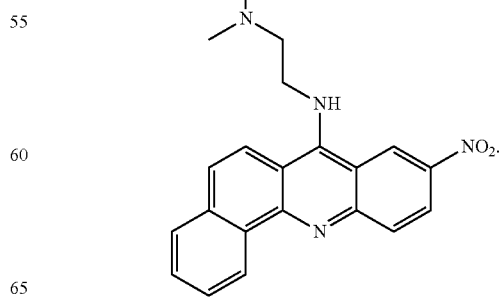

18. The compound of claim 17, which is
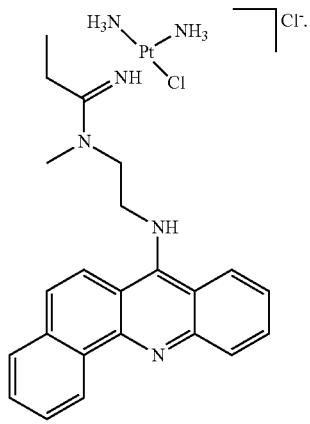
19. The compound of claim 17, which is
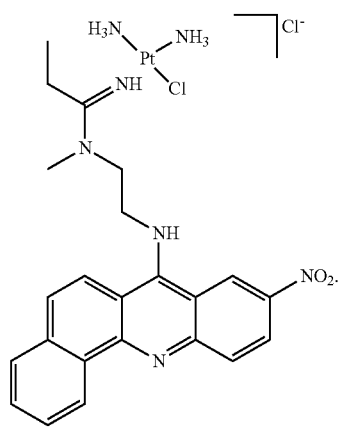
* * * * *